(12) United States Patent
Barrett et al.

(10) Patent No.: US 9,811,438 B1
(45) Date of Patent: Nov. 7, 2017

(54) TECHNIQUES FOR PROCESSING QUERIES RELATING TO TASK-COMPLETION TIMES OR CROSS-DATA-STRUCTURE INTERACTIONS

(71) Applicants: Ryan Barrett, San Francisco, CA (US); Katsuya Noguchi, San Francisco, CA (US); Nishant Bhat, San Francisco, CA (US); Zhengua Li, Saratoga, CA (US); Kurt Smith, San Francisco, CA (US)

(72) Inventors: Ryan Barrett, San Francisco, CA (US); Katsuya Noguchi, San Francisco, CA (US); Nishant Bhat, San Francisco, CA (US); Zhengua Li, Saratoga, CA (US); Kurt Smith, San Francisco, CA (US)

(73) Assignee: COLOR GENOMICS, INC., Burlingame, CA (US)

( * ) Notice: Subject to any disclaimer, the term of this patent is extended or adjusted under 35 U.S.C. 154(b) by 0 days.

(21) Appl. No.: 15/592,949

(22) Filed: May 11, 2017

Related U.S. Application Data

(63) Continuation of application No. 15/366,409, filed on Dec. 1, 2016, now Pat. No. 9,678,794.
(Continued)

(51) Int. Cl.
*G06F 9/46* (2006.01)
*G06F 11/34* (2006.01)
(Continued)

(52) U.S. Cl.
CPC ........ *G06F 11/3419* (2013.01); *G06F 9/4887* (2013.01); *G06F 11/3024* (2013.01); *G06N 99/005* (2013.01)

(58) Field of Classification Search
None
See application file for complete search history.

(56) References Cited

U.S. PATENT DOCUMENTS

| | | | |
|---|---|---|---|
| 6,708,184 B2* | 3/2004 | Smith | G06F 17/30017 |
| 2015/0269244 A1* | 9/2015 | Qamar | G06F 17/30598 |
| | | | 705/7.42 |
| 2015/0269433 A1* | 9/2015 | Amtrup | G06Q 20/3276 |
| | | | 382/115 |

OTHER PUBLICATIONS

U.S. Appl. No. 15/366,409, filed Dec. 1, 2016, Notice of Allowance dated Feb. 22, 2017, all pages.

* cited by examiner

*Primary Examiner* — Sisley Kim
(74) *Attorney, Agent, or Firm* — Kilpatrick Townsend & Stockton LLP

(57) ABSTRACT

Methods and systems disclosed herein relate generally to data processing by applying machine learning techniques to iteration data to identify anomaly subsets of iteration data. More specifically, iteration data for individual iterations of a workflow involving a set of tasks may contain a client data set, client-associated sparse indicators and their classifications, and a set of processing times for the set of tasks performed in that iteration of the workflow. These individual iterations of the workflow may also be associated with particular data sources. Using the iteration data, anomaly subsets within the iteration data can be identified, such as data items resulting from systematic error associated with particular data sources, sets of sparse indicators to be validated or double-checked, or tasks that are associated with long processing times. The anomaly subsets can be provided in a generated communication or report in order to optimize future iterations of the workflow.

20 Claims, 5 Drawing Sheets

Related U.S. Application Data

(60) Provisional application No. 62/262,183, filed on Dec. 2, 2015.

(51) Int. Cl.
*G06F 9/48* (2006.01)
*G06N 99/00* (2010.01)
*G06F 11/30* (2006.01)

TECHNIQUES FOR PROCESSING QUERIES RELATING TO TASK-COMPLETION TIMES OR CROSS-DATA-STRUCTURE INTERACTIONS

CROSS-REFERENCES TO RELATED APPLICATIONS

This application is a continuation of U.S. Nonprovisional application Ser. No. 15/366,409, filed Dec. 1, 2016, which claims the benefit of and the priority to U.S. Provisional Application No. 62/262,183, filed on Dec. 2, 2015. Each of these applications is hereby incorporated by reference in its entirety for all purposes.

FIELD

Methods and systems disclosed herein relate generally to the integration and analysis of data using machine learning techniques. More specifically, a comprehensive data set associated with various iterations of a workflow can be used to determine one or more anomaly subsets of that comprehensive data set based on various factors associated with each workflow iteration. Based on various goals, different anomaly subsets can be identified and reported in order to optimize and improve future iterations of the workflow.

BACKGROUND OF THE INVENTION

Data is being generated and processed at an exponentially increasing rate. However, this increased rate of data generation and processing can result in many errors or inefficiencies arising during the generation and processing of that data. Unfortunately, these errors or inefficiencies can be difficult to identify due to the sheer amount of data involved.

There exists a need for techniques to integrate a large volume of data and analyze it to reliably determine errors or inefficiencies associated with the generation and processing of all that data. The identification of these errors or inefficiencies can be used in order to improve the accuracy and efficiency in generating and processing future data.

BRIEF SUMMARY OF THE INVENTION

In some embodiments, various computer-implemented systems and methods are disclosed for using machine learning to identify anomaly subsets of iteration data. The actions in the method, or performed by the system, can include accessing a structure including at least part of a definition for a workflow, the workflow including: a first task of accessing a set of reads based on a material associated with a respective client; a second task of aligning each read of the set of reads to a portion of a reference data set; a third task of generating a client data set for the respective client using the aligned set of reads, the client data set including a set of values associated with each of one or more units, each unit of the one or more units corresponding to a set of defined positions within a data structure; a fourth task of detecting a presence of one or more sparse indicators associated with the respective client by comparing the set of values of the client data set to corresponding values in the reference data set, each sparse indicator of the one or more sparse indicators identifying a distinction between the client data set and the reference data set; and a fifth task of classifying each sparse indicator of the one or more sparse indicators based on a state transition likelihood associated with that sparse indicator. In some of such embodiments, the actions may further comprise accessing iteration data for the workflow, the iteration data including, for each client of a plurality of clients, a result corresponding to a partial or full performance of the workflow and an iteration identifier; using a machine-learning technique to process the iteration data to identify an anomaly subset of the iteration data; and generating a communication that represents the anomaly subset.

In some embodiments, the result corresponding to the partial or full performance of the workflow includes, for each task of a plurality of tasks of the workflow, a processing-time variable that indicates when a performance of the task was completed or a duration of performance of the task. In some of such embodiments, the anomaly subset of the iteration data identified using the machine-learning technique identifies a task of the plurality of tasks associated with long processing times relative to past processing times or normalized or unnormalized processing times of one or more other tasks of the plurality of tasks.

In some embodiments, the result corresponding to the partial or full performance of the workflow identifies one or more sparse indicators associated the client, such that the iteration data identifies a plurality of sparse indicators. In some of such embodiments, the anomaly subset of the iteration data identified using the machine-learning technique identifies a subset of the plurality of sparse indicators. In some of such embodiments, the communication facilitates selective confirmatory processing to be performed to determine whether data corresponding to the subset of the plurality of sparse indicators is validated.

In some embodiments, the iteration data further includes, for each client of the plurality of clients, an origination identifier associated with a source of the set of reads and a timestamp. In some of such embodiments, using the machine-learning technique to process the iteration data includes determining whether results corresponding to a first origination identifier are statistically different than results corresponding to one or more second origination identifiers or than results corresponding to a prior time period and the first origination identifier. In some of such embodiments, the communication identifies the source associated with the first origination identifier.

In some embodiments, the iteration data further includes, for each client of a plurality of clients, one or more data-source variables that identify or characterize a source of the iteration data. In some of such embodiments, using the machine-learning technique includes updating or generating a model to identify data-source variables predictive of the results.

In some embodiments, using the machine-learning technique comprises retrieving a parameter for a machine-learning model trained on another iteration data, the parameter reflecting a degree of variability observed across clients, iterations or alignment positions; determining whether, for each portion of multiple portions of the iteration data, an observed variability for the portion corresponds with the parameter; and for each portion of the multiple portions for which it is determined that the observed variability for the portion does not correspond with the parameter, identifying the portion as an anomaly subset.

In some embodiments, the actions in the method, or performed by the system, further comprise receiving, from a source, a request to perform an anomaly-detection assessment, wherein the iteration data is accessed and processed in response to receiving the request; and availing the communication to the source. In some embodiments, the source may be a user and receiving the request may correspond to receiving input from the user. In some embodiments, the source may be a device.

BRIEF DESCRIPTION OF THE DRAWINGS

The present disclosure is described in conjunction with the appended figures.

Figure 1:
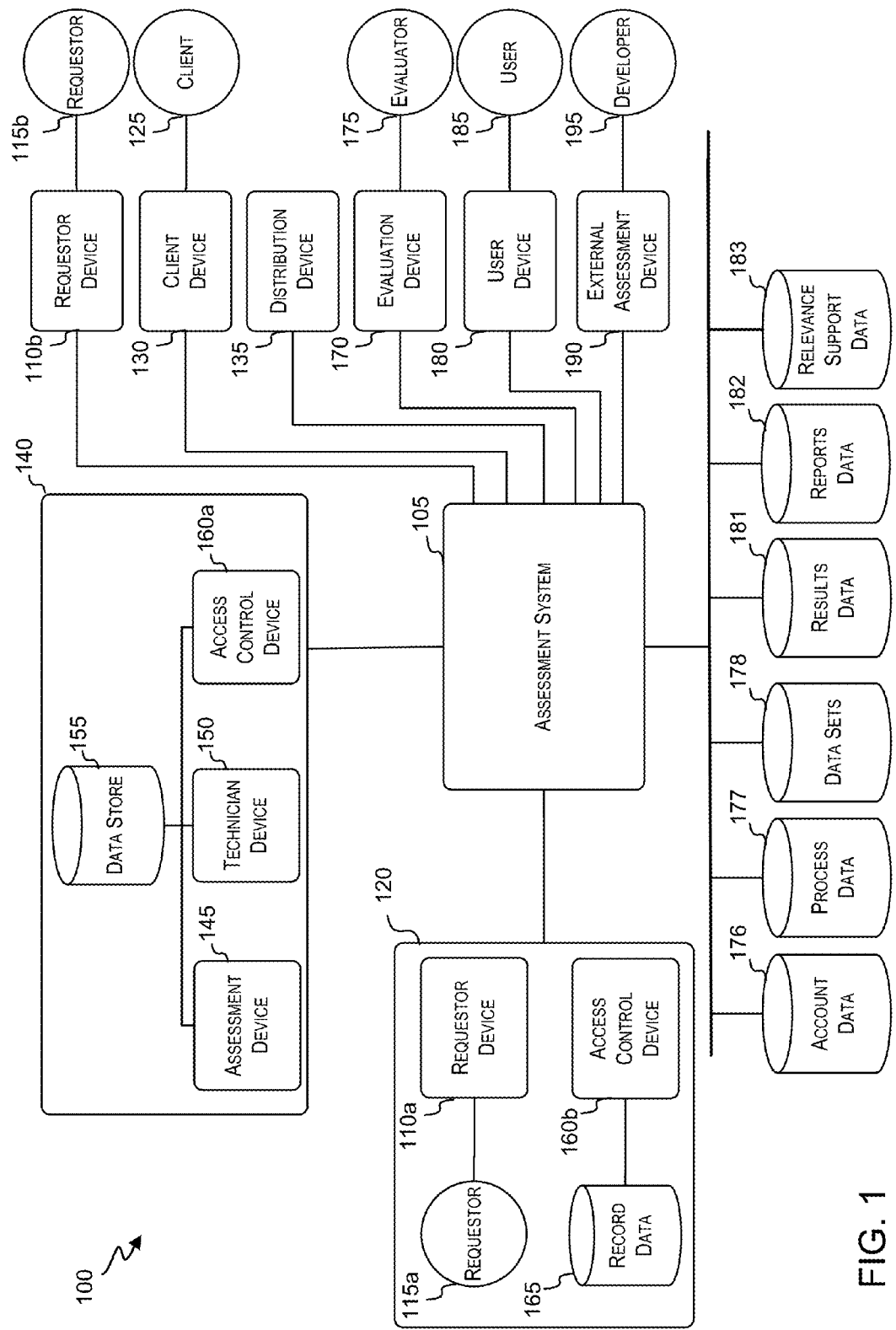
FIG. 1 shows a representation of a data processing network, in accordance with some embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

Many systems involve the processing of large volumes of data, which may include steps for generation, integration, aggregation, and analysis of that data. However, in order for any analysis to provide useable results that are accurate, each step in the processing of data needs to be relatively error-free. Additionally, there is frequently a demand that any analysis provides results quickly—necessitating each step in the processing of data to be performed relatively quickly and efficiently while still remaining relatively error-free.

Accordingly, it should be noted that the identification of anomaly subsets of large volumes of data used in processing can lead to the identification of any sources of error or inefficiencies that arise in the processing of that data. For instance, the data can contain measurements which may be expected to be within a certain range of values. Spotting and identifying anomalous measurements would allow shared characteristics between those anomalous measurements to be identified, such as the identification of a single source producing those anomalous measurements. As another example, the data may contain processing times associated with various steps in the processing of the data. Processing times for different processing steps may also be expected to be within a certain range of values. Spotting and identifying anomalous processing times would highlight the steps associated with those anomalous processing times. This allows for the identification of steps in the data processing that are taking too long. In order to identify the anomaly subsets of large volumes of data, machine-learning techniques described herein can be employed to perform big-data analysis. The identification of anomalous subsets of large volumes of data can be used to generate communications and/or reports that can be interpreted to alter and improve the data processing to reduce those errors and inefficiencies.

In some embodiments, the various steps involved in the processing of data may be referred to as processes or tasks, and they may be collectively referred to as a workflow. Thus, a workflow may include multiple tasks for processing data. In some cases, these workflows may be repeated. Accordingly, the systems and methods herein may be applied to any possible workflows, particular iterations of a workflow, and/or any set of tasks within a workflow in order to identify sources of error or inefficiencies within those workflows.

However, in order to facilitate understanding of the systems and methods described herein, this application describes the systems and methods using example workflows for the analysis of genetic data taken from lab samples. Explanations and descriptions of workflows, processes, types of anomaly subsets of data that may be identified (and their purposes), methods of identification of those anomaly subsets, as well as various sources of errors and inefficiencies within the workflows, are described in relation to such example workflows. However, these various examples are not intended to be limiting on the disclosure and the potential applications of the systems and methods described herein.

From that perspective, in some embodiments, data may be aggregated and analyzed in order to identify errors or bottlenecks likely to be experienced during particular iterations of a workflow that includes multiple tasks for analyzing genetic data taken from lab samples. These workflows and the tasks within those workflows are described in further detail later in this disclosure; however, as an introductory matter, these workflows may include tasks for: collecting inputs from a subject, sending a sample-collection kit, receiving a sample, sequencing the sample, detecting any sparse indicators from the sequence, categorizing any sparse indicators, sending a sample to an external lab for confirmatory testing (for positive test results), and generating variables or likelihoods based on any sparse indicators. These workflows may also include tasks for generating and providing reports that identify these variables or likelihoods, and/or provide counseling. These workflows may also include tasks for identifying an anomaly subset of the data used in the workflow, generating and providing communications that identify the anomaly subset, and/or providing suggestions on how the workflow may be improved or optimized. Some of these tasks may be conditional, in that they may only need to be performed upon detecting that a particular condition has occurred (e.g., a sparse indicator of a certain assignment or classification was detected). These workflows may be repeatedly performed for various subjects and/or clients, whose lab samples are used in the generation of data used in the workflows. In some embodiments, any individual iteration of the workflow may be an instance of the workflow that is performed on a particular lab sample belonging to a single client.

In order to actually identify an anomaly subset of the data used in a workflow for analyzing genetic data taken from lab samples, various machine-learning techniques may be applied. Although any known machine-learning technique may be used, the exact machine-learning techniques applied may depend on the anomaly subset being identified since specific machine-learning techniques may confer advantages for determining certain anomaly subsets. Various machine-learning techniques, along with various anomaly subsets of data that can be identified using them, are described in greater detail throughout this application; however, a brief introduction to them is provided immediately below:

A first example of determining an anomaly subset of data includes determining tasks for various iterations of the workflow that are taking a long processing time relative to the past processing times for completing that task, or taking a long processing time relative (either normalized or unnormalized) to the processing times of one or more other tasks in the workflow.

These implementations may involve the system monitoring data and/or communications that are indicative of a task start time and/or a task completion time for each task performed in an iteration of a workflow. From this information, a processing time or a turnaround time may be identified for each completed task in an iteration of a workflow. Alternatively, the system may monitor data and/or communications that are directly indicative of the turnaround processing time of tasks performed in an iteration of the workflow. This allows processing times to be known for every task performed in every iteration of the workflow. Each iteration of the workflow may be associated with a particular subject or client (e.g., those for which samples were processed at a given laboratory or by a given device), and there may be data available for many iterations of the workflow. Thus, processing times for a specific task in the workflow can be taken from many iterations to be aggregated and compared. In other words, processing times may be aggregated across some or all subjects for a given task and analyzed using machine-learning techniques and big-data analysis. Examples of analysis that can be performed include identifying outlier processing times from the group, comparing processing times for a task to standard processing times for that task observed in the past, comparing processing times for a task to processing times for other tasks in the workflow, and so forth. Various statistics can also be generated on the processing times (e.g., mean, median, standard deviation, outlier count, etc.). All of this information may be used to generate a presentation, report, or communication which may identify an anomaly subset of processing times and their associated tasks that are suspected of deviating from normal process times, which may then be sent to a user in order to detect tasks (or laboratories, devices, time periods, or geographies) associated with processing delays.

A second example of determining an anomaly subset of data includes determining that data from a first data origin/source is statistically different from data from a second data origin/source. For instance, genomic data may be collected at different laboratories or using different pieces of equipment (e.g., following equipment replacement) at a laboratory. Different equipment can produce data with different biases, scientific units, etc. Alternatively, the first data origin/source may generate data that is different from what is expected. For example, in some instances, an instrument that generates data used in processing may not be calibrated properly, which may lead to generated measurements that systematically deviate from the measurements that instrument would generate if it were calibrated properly. Alternatively, data originating from a same device may, in time, exhibit different biases, units, and so on, which may be a result of a manipulation of a control of the device and/or equipment wear. Or the data may be the result of using different protocols and/or data interpretation techniques with data-generating instruments, which may also lead to the generation of data with different biases, units, variables, and so on, from what is expected.

The implementations used may depend on whether data from a first data origin/source is being compared with some baseline (such as a set of control data, or past data generated by that data origin) or against data from a second data origin/source. Additionally, the implementation may also involve the system identifying a reason that data from a data origin/source is statistically different from what is expected. To do so, the system may use machine-learning techniques and big-data analysis in order to detect trends in equipment outputs and/or differences in equipment outputs. For example, cluster analyses can identify trends in cluster centers or sizes and/or can identify clusters that correspond to or may represent differences between laboratories or pieces of equipment. The system may then perform actions based on the identified reason for data from a data origin/source being different from what is expected. For example, if the system detects faulty equipment (e.g., via outlier detection), the system may provide a communication or a recommendation to a user to fix that equipment. Or, if the system detects that the measurements from the faulty equipment are due to systematic, repeatable error, the system may be able to automatically determine and apply adjustments to correct those measurements. However, if the data being received from the data origin/source is in the wrong scientific unit, the system may instead determine a set of conversion and/or normalization metrics to be applied to data, and then perform an automated unit conversion and/or normalization. Thus, in many embodiments, the system may use machine-learning to automatically determine the reason for errors in data received from a given laboratory or device, and then apply an adjustment (such as an automated unit conversion and/or normalization) in order to fix those errors.

A third example of determining an anomaly subset of data includes determining one or more sparse indicators in a plurality of sparse indicators that need validation. Additional information and examples on how data sets may be evaluated to detect, assess, and classify sparse indicators can be found described in U.S. Non-Provisional patent application Ser. No. 15/163,191, titled "UNIT-SPECIFIC DATA REPOSITORY QUERIES FOR RESTRICTED PROCESSING OF EXTERNAL ASSESSMENT SYSTEM REQUESTS", filed May 24, 2016, which is hereby incorporated by reference in its entirety for all purposes. In the example workflows for analyzing genetic data from lab samples, a client data set can be compared against a reference data set in order to identify a plurality of sparse indicators, with the sparse indicators representing differences between the client data set and the reference data set. Frequently, the workflow may further attempt to classify each of the sparse indicators. This classification can be performed using a lookup of existing knowledge or based on more complex methods, such as through a predictive model. Thus, this classification may not always be completely accurate due to errors that arise in identifying the sparse indicator, as well as errors that arise in classifying it.

In order to mitigate these errors, some sparse indicators are picked to be sent out for double-checking and confirmation. In some embodiments, the client data set may generated again using more expensive and more accurate equipment in order to double-check any sparse indicators that need to be confirmed. In some embodiments, an identified sparse indicator may be correct but the classification assigned to that sparse indicator may need to be double-checked. These types of validations may not necessarily require that the client data set be generated again. However, in either case, the validation of every single sparse indicator (either for accuracy or classification) would be inefficient and time—consuming. Instead, machine-learning techniques and big-data analysis can be used to selectively determine sparse indicators for validation. For example, a machine-learning model can be trained based on a number of inputs and characteristics of sparse indicators. This model can be used to determine which sparse indicators are predicted to be accurately identified and require no further validation. The model can also be used to select sparse indicators that likely need to be double-checked and validated for accuracy and/or classification. Since the validation of sparse indicators can be an automated task in the workflow, the selective prediction of an anomaly subset of sparse indicators that require additional validation—as opposed to subjecting all of the sparse indicators to validation—can improve the efficiency of that task and the overall workflow.

Overview and Context—FIG. 1

With regards to the figures, FIG. 1 shows a representation of an assessment network 100, which may include any combination of the various systems or components shown. An overview of the interactions between the various components of assessment network 100 are described below.

In some embodiments, the assessment network 100 may include an assessment system 105 capable of receiving an electronic request from a requestor device 110. The assessment system 105 may include one or more electronic devices (e.g., storage devices, servers, and/or computers) and may, but not need, reside partly or entirely at a remote server. A requestor device 110 may be configured and located to receive input from a requestor 115. In some embodiments, a requestor device 110*a* is located in an external facility 120. In some embodiments, a requestor device 110*b* includes an internally linked requestor device 110*b*, such as one that itself receives invitations to generate electronic requests. The invitations received by the requestor device 110*b* may come from any source, including the assessment system 105.

The electronic request received by the assessment system 105 from the requestor device 110 may include instructions to conduct a data-set analysis, for example. Optionally, such an electronic request may be encrypted prior to transmission and decrypted upon receipt. In some embodiments, the electronic request may identify, or otherwise indicate, one or more states to be evaluated during the analysis and/or during an assessment. In some embodiments, the electronic request may identify a client and/or include additional data pertaining to the client, such as client-identifying data.

In some embodiments, the aforementioned client may be the client 125. In some embodiments, the client may be equated to, by the assessment system 105, a client device 130. In some instances, a client device 130, associated with the client 125, initially transmits a preliminary electronic request for the analysis and/or assessment to assessment system 105. For example, such a preliminary electronic request may be initiated via interaction with a website associated with the assessment system 105. The same or a subsequent preliminary request may identify a particular requestor (e.g., by name, office location, phone number, and/or email address) and/or may request that a requestor, such as a requestor 115*b* associated with an internally linked requestor device 110*b*, submit such a request.

When a particular entity is identified in a preliminary electronic request, the assessment system 105 may identify a destination address (e.g., IP address or email address) associated with the entity and transmit a communication identifying information associated with the preliminary request (e.g., the client, a type of analysis, and so on). The communication may include a partial instruction and/or an input field that would confirm that the request of the client 125 is to be generated and transmitted back to the assessment system 105. Such a communication may facilitate receipt of the electronic request from the requestor device 110*b* by the assessment system 105.

When it is requested that a requestor, such as a requestor 115*b*, associated with an internally linked requestor device 110*b* submit such a request, the assessment system 105 may transmit a similar communication to a requestor device 110*b* that may have been selected from among multiple internally linked requestor devices. The selection may be based on a load balancing technique, availability hours, expertise, locations of the multiple requestor devices, a pseudo-random selection technique, and/or an entity affiliation.

Once the electronic request has been received from a requestor device 110 (e.g., in response to a preliminary request from a client device 130) by the assessment system 105, the assessment system 105 may evaluate the request to ensure that all required data has been provided and that all required data pertaining to the client 125 has been identified (e.g., via the request, a preliminary request and/or stored data). If the assessment system 105 determines that all required information has not been identified, an additional request for missing information may be transmitted back to the requestor device 110 and/or the client device 130. In response, an updated electronic request with the updated information may be transmitted back to the assessment system 105. In various instances, an object provided to a user depends on an analysis requested, whether, and what kind of, new data-generation processing of a material is required for the analysis, a number of data-set units being assessed (e.g., and whether they have been previously assessed), a number and/or type of analyses being requested, a number and/or type of analyses previously requested, a number and/or type of analyses predicted to be requested subsequently, a state for which a progression prediction is being requested, whether a user is granting other entities' access to the client's data or results, whether a user is authorizing additional analyses to be performed on the client's data, and/or whether a user is granting permission to send offers to request user access to results or reports other than those initially being requested.

When all required information has been provided to the assessment system 105, the assessment system 105 may send an instruction communication to a distribution device 135. Optionally, that instruction communication may be encrypted prior to transmission; such an encrypted communication may be decrypted upon receipt. Optionally, that instruction communication may be transmitted over one or more network links, such as including transmission, at least in part, over a public communications network, such as the Internet. That instruction communication may include, for example, a name and address of the client 125 and, in some instances, an indication as to what is to be provided to the client 125 for collection of a material for subsequent analysis. For example, an initial electronic request received by the assessment system 105 may indicate a type of analysis that is to be performed on a material (e.g., an analysis pertaining to a likelihood of getting one or more particular types of states) and/or a type of material (e.g., type of sample) that is to be analyzed. This instruction communication sent by the assessment system 105 may identify the type of analysis, type of material, and/or kit associated with collection of the material. The instruction communication may thus facilitate and/or trigger a physical distribution of instructions, which may include a kit or other sample collection materials, to a client address. The instructions may include, for example, instructions as to how to collect a material, a container for storing the material and/or information pertaining to an instruction or type of analysis to be conducted. Alternatively, the instructions may be provided to a facility, such as the external facility 120 associated with a requestor 115a, that may aid client 125 in obtaining the material.

When the client 125 provides the material, the material may then be directed to and received at a data generator 140 in order for analysis to be performed. In some embodiments, the data generator 140 may be part of a facility. In some of such embodiments, the data generator 140 may include one or more assessment devices 145 configured to generate data reads, data elements, or data sets for various data-set units using the material received from the client 125. For example, in some embodiments the assessment device 145 may include a data-characterizer device (e.g., sequencer and/or polymerase chain reaction machine). Such a data-characterizer device can be used with the material received from the client 125 to generate a set of data reads.

In some embodiments, the data generator 140 may further include one or more technician devices 150, such as a desktop or laptop computer. In some embodiments, various components of the data generator 140 may be used to generate data. For example, data may be generated by one or more devices (e.g., one or more of the assessment device 145 and/or technician device 150). The generated data may be stored at a data store 155, which may be remote from all the data generator device or part of a data generator device. The data may, for example, include identifying client information (e.g., a name and address), facility information (e.g., location and name), device specifications (e.g., manufacturer and model of assessment device) and data. In some embodiments, a facility, such as external facility 120 or data generator 140, may correspond to a lab.

In some instances, data is optionally collected or requested from one or more external systems. Thus, assessment system 105 may transmit one or more other data requests and one or more other data transmissions may provide the other data. For example, one or more data sets and/or one or more processed versions thereof (e.g., identifying one or more sparse indicators) corresponding to an existing or new client may be received from an external system. As another example, the assessment system 105 may transmit a client data set to an external system, and the external system may then return a result of an assessment of the client data set. As yet another example, other data may include a data set (or results based on such data) corresponding to another individual (e.g., an entity related to a client and/or an entity sharing a characteristic with a client). The other individual may be, for example, identified based on input from the client and/or automatically identified (e.g., based on a query of a data store to identify clients associated with inputs or results indicating a shared characteristic or relationship). In some instances, a state assessment variable may be generated based on data from multiple other people, and the data for each other person may be weighted based on (for example) how closely related the person is with a client and/or how many or which characteristics the person shares with a client.

In some embodiments, the data generator 140 may include an access control device 160a which may control which devices and/or entities may gain access to the generated data. These access control restrictions may apply to devices and/or entities internal to the data generator 140 and/or to devices and/or entities external to the data generator 140. Access control device 160a may implement one or more rules, such as restricting access to client data to one or more particular devices (e.g., associated with assessment system 105). Such access may further or alternatively be controlled via logins, passwords, device identifier verification, etc.

In various instances, access control device 160a controls access via control of pushed transmissions and/or via control of processing pull requests. For example, a rule may indicate that data pertaining to a material, such as a sample, is to automatically be transmitted to a particular assessment system 105 (and/or device associated therewith) upon completion of a facility-based assessment or detection of particular data (e.g., data matching a request). Access control device 160a may then monitor for such a criterion to be met and may then generate and transmit appropriate data.

The generated data may include a plurality of data reads, data elements, or sets (e.g., each data read in the plurality of data reads corresponding to a same client, or at least some of the plurality of data reads corresponding to different clients). In various instances, the data may be transmitted to the assessment system 105 in a batch-mode, in a streaming mode, in real-time as data is produced, and/or upon request. The data may also be stored at a data store local or remote to the data generator 140. A given transmission or stream may include data that corresponds to a single, or in other instances to multiple, client, sample, and/or data reads. In some instances, the access control device 160a evaluates one or more transmission conditions, which may indicate, for example, whether and/or what data is to be transmitted given a quantity of data collected (e.g., generally, since a past transmission and/or for a given client or sample) and/or given a time since a previous transmission. In one instance, as data reads are generated by an assessment device, a data set is generated so as to include each new data read and one or more identifiers (e.g., of a client, sample, time and/or facility device). The data may then be transmitted via a discrete communication (e.g., via FTP, over a webpage upload, email message, or SMS message) to assessment system 105. In one instance, the data may then be appended to a stream that is being fed to the assessment system 105.

It will be appreciated that the assessment network 100 may, in some instances, include multiple data generators 140, each of which may include any combination of an assessment device 145, technician device 150 and/or access control device 160a. Further, a given data generator 140 may, in some instances, include multiple assessment devices 145, multiple technician devices 150 and/or multiple access control devices 160a. Thus, data received at assessment system 105 may include data collected by and/or derived from data collected by different assessment devices, which may result in the data having different biases, units, and/or representation. Similarly, personnel operating different technician devices 150 may utilize different protocols and/or data interpretation techniques, which may again result in receipt of data at assessment system 105 that has different biases, units, variables, and so on. Further, even data originating from a same device may, in time, exhibit different biases, units, and so on, which may be a result of a manipulation of a control of the device and/or equipment wear.

Thus, in some instances, the assessment system 105 performs a comparison across data received from a data generator device (e.g., an access control device 160a or directly from an assessment device 145 or technician device 150) associated with data generator 140. The comparison may be across, for example, data collected at different facilities, data based on measurements collected at different devices, and/or data collected at different times. In some embodiments, the assessment system 105 performs a comparison across data received from different devices, such as devices associated with multiple data generators 140. It will be appreciated that the comparison may include a direct comparison of collected data or comparing preprocessed versions of the collected data. For example, received data may first be preprocessed via a transformation and/or dimensionality-reduction technique, such as principal component analysis, independent component analysis, or canonical correspondence analysis.

The comparison may include, for example, performing a clustering technique so as to detect whether data corresponding to a given facility, device, or time period predominately resides in a different cluster than data corresponding to one or more other facilities, devices, or time periods. The clustering technique may include, for example, a connectivity based clustering technique, a centroid-based clustering technique (e.g., such as one using k-means clustering), a distribution-based clustering technique, or a density-based clustering technique.

The comparison may additionally or alternatively include a statistical technique, such as one that employs a statistical test to determine whether two or more data sets (e.g., corresponding to different facilities, devices, or time periods) are statistically different. For example, a Chi-square, t-test or ANOVA may be used.

The comparison may additionally or alternatively include a time-series analysis. For example, a regression technique may be used to determine whether output from a given device is gradually changing in time.

When it is determined that particular data corresponding to a given facility, device, or time period is different than data corresponding to one or more other facilities, devices, or time periods (e.g., is assigned to a different cluster than other data or is associated with a p-value below a threshold), a normalization and/or conversion factor may further be identified. For example, a normalization and/or conversion factor may be identified based on centroids of data clusters and/or inter-cluster distances. As another example, a linear or non-linear function may be derived to relate data from a given facility, device, or time period to other data.

In some instances, a determination that particular data corresponding to a given facility, device, or time period is different than data corresponding to one or more other facilities, devices, or time periods may indicate that data from the given facility, device, or time period is not to be used. In such instances, an instruction communication may be sent to a facility to reprocess a material, such as a sample.

In addition to receiving data from a data generator 140, the assessment system 105 may further collect one or more other data that may be used to assess, for example, a likelihood for transitioning into a particular state. For example, one type of other data may include inputs provided at a client device 130, such as inputs that indicate past-state data and/or current-state data, familial-state data and statuses, age, occupation, activity patterns, association with environments having particular characteristics, and so on. The other data may be received by way of one or more other data transmissions from an external system. In some embodiments, this data transmission may be encrypted prior to transmission and/or decrypted upon receipt. Optionally, this data may be transmitted over one or more network links, such as including transmission, at least in part, over a public communications network, such as the Internet.

Another type of other data may include data automatically detected at a client device 130. For example, a wearable client device may track activity patterns so as to estimate calories burned per day, or the wearable client device may estimate a pulse distribution, client temperature, sleep patterns and/or indoor/outdoor time. This data obtained directly by client device 130 may be directly transmitted (e.g., after a request and/or authorization handshake) to assessment system 105 and/or via another client device (e.g., via accessing health-data on a phone or computer device). Optionally, other data obtained directly by client device 130 may be transmitted over one or more network links, such as including transmission, at least in part, over a public communications network, such as the Internet. Optionally, other data obtained directly by client device 130 may be transmitted over at least a portion of a communication system. Optionally, other data obtained directly by client device 130 may be part of another data transmission.

Yet another type of other data may include record data, which may be stored, for example, at a record data store 165 at and/or associated with an external facility, such as one having provided an electronic request to perform an analysis or assessment pertaining to a client and/or one as identified via input at a client device 130. To illustrate, the other data may identify one or more client reported experiences and/or evaluation results for a client or may include a result of one or more tests.

In some instances, other data may include data pertaining to a different client. For example, it may be determined or estimated that a given client is related to another client. Such determination or estimation may be based on inputs detected at a client device identifying one or more family members (e.g., by name), and a data store may be queried to determine whether any clients match any of the family member identifications. Such relationship determination or estimation may alternatively or additionally be based on a data set analysis, such that a raw or processed data set from the given client is compared to a raw or processed data set from some or all other clients to identify, for example, whether any other clients share a threshold portion of a data set with the client. Upon detecting an above-threshold match, a percentage of value matching may be used to estimate a type of relationship between the clients. Upon identifying a related client, other data corresponding to the related client may be identified. For example, the other data may include a past or current state of the related client. The other data may be identified (for example) based on an input provided by the client or the related client or record data associated with the related client.

Thus, the assessment system 105 may have access to, for a given client, one or more data sets, data set availability modification data, client-reported data, record data, test data, activity data, and/or other types of data. These various types data may be detected, assessed, or otherwise evaluated, such as in one or more assessment processes. The detection and/or assessment may be performed, for example, partly or fully at assessment system 105. In some instances, the detection and/or assessment is performed in a partly or fully automated manner. In some instances, the detection and/or assessment involves processing of inputs provided by a reviewer or evaluator.

Through the interaction of multiple devices and entities, an assessment system 105 may receive data sets corresponding to individual clients. As illustrated, assessment system 105 may connect to each of one or more other systems or devices, using any method of communication or data exchange known in the art. For example, the assessment system 105 may communicate to other component within the assessment network 100 using a wired or wireless data connection that makes use of or is compliant with one or more Institute of Electrical and Electronics Engineers (IEEE) networking standards, such as 802.3 (Ethernet), 802.11 (Wi-Fi), or 802.16 (WiMAX), or other data communications standards such as IEEE 1394 (FireWire), Bluetooth, Universal Serial Bus (USB), Serial ATA (SATA), Parallel ATA (PATA), Thunderbolt, Fibre Channel, Small Computer System Interface (SCSI), GSM, LTE, etc. The data connections used may include one or more TCP/IP compliant interconnections, such as may be present on a private or public communications network, such as the Internet. The data connections may represent or include one or more intermediate systems or data connections between various other components of assessment network 100.

Upon detecting such a deviation or combination (or a threshold quantity thereof), the particular deviation and/or combination may be identified in a review-request communication and transmitted to an evaluation device 170. Evaluation device 170 may then present the identification to an evaluator 175 and detect input that is indicative of an estimated likelihood to associate with the deviation and/or combination, for example, as part of an optional review analysis process. A review-request response may be transmitted from evaluation device 170 to assessment system 105, for example, to provide the results of any review or input generated by an evaluator 175. The data included in review-request response may be used in report generation and may be included and/or otherwise influence the content of the final report transmitted in a report transmission.

A result generated by assessment system 105 may include a quantitative or qualitative (e.g., categorical) likelihood variable, such as one corresponding to a transitioning to a particular state. For example, the likelihood variable may include a percentage probability or range of transitioning into a particular state. As another example, the likelihood variable may be partitioned into three categories.

Assessment system 105 may generate an electronic report, that includes the result and/or that is selected based on the result. A report communication or transmission may include the report and be transmitted to client 125 or facility 120, such as by way of client device 130 or requestor device 110a. As an example, a report may identify one or more sparse indicators detected in a client data set and/or a bucket of each of one or more sparse indicator. A report may identify a likelihood (e.g., numeric or categorical) of transitioning to a particular state and/or a technique for having generated such a result. A report may identify types of data (e.g., particular data-set units and/or other type of data) used in the analysis. A report may identify a confidence in a result (e.g., a likelihood variable). A report may identify a recommendation (e.g., to contact a requestor or to receive a particular test or evaluation).

In some instances, a report must be approved (e.g., by a requestor 115a or 115b) before it is transmitted to a client device 130. A report-reviewing interface may, but need not, include a configuration to allow a reviewing entity to change or add to the report. A report-reviewing interface may further allow or require a reviewing entity to identify a time at which to send the report to a client.

Assessment system 105 may update and may have access to a variety of data stores, part or all of which may be remote from, co-localized with assessment system 105, and/or included in assessment system 105. One or more of the data stores may include a relational data store, such that data from one data store or structure within a data store may be used to retrieve corresponding data from another data store or structure.

Each of one, more, or all of the data stores may be associated with one or more access constraints. Access constraints applicable to a given data store may be stored as part of the data store or separately (e.g., in an access control data store). Access constraints that apply to one type of data may differ from access constraints that apply to another type of data. For example, account and client data may be associated with stricter access constraints than results data, to make it more difficult for a user, developer, or hacker to be able to link data to a particular individual. An access constraint may identify one or more individuals, devices, systems, and/or occupations permitted to access some or all data in a data store. An access constraint may include a rule, such as one that indicates that a user is permitted to access data pertaining to any of a group of users that the entity was involved in with respect to a transfer of a kit, or that indicates that any low-level authorized user is permitted to access de-identified data but not identifiable data, or that indicates that a high-level authorized user is permitted to access all data. As another example, access constraints may indicate that process data is to be hidden from external developers and available to internal users; that data-set unit, sparse indicator, and data set availability data is to be made available to all authorized external developers and internal users; and that client data is to be availed to authorized internal users and only availed to external developers to the extent to which each corresponding users represented in the data is a user of the developer (e.g., and that the client authorized such data access).

When different access rights apply to different types of data, a query protocol may be established to address instances where a query relates to each type of data. For example, a query may request Variable X for each client corresponding to Data Y, and Variable X and Data Y may correspond to different access constraints. As another example, a query may request a count of clients for which both Data Y and Data Z was detected, and Data Y and Z may correspond to different access constraints. One example of a query protocol is to use a most restrictive overlap of data constraints applying to the query. Another example of a query protocol is to permit use of an at least partly more relaxed access constraint so long as it relates to defining a client set or state and not to results to be returned or processed.

In some instances, an access constraint is configured to inhibit an identification of particular data (e.g., client identity). Such a constraint may relate to a precision of requested data. To illustrate, a constraint may be configured to permit a user to request and receive data identifying client locations, so long as the request is configured to not request too specific of a location and/or so long as the request corresponds to a number of client data elements sufficiently large to obscure (e.g., in a statistical result) a precise location. Compound queries may be more sensitive to potential identification concerns, such that one or more access constraints are configured to permit access to less precise data when multiple data elements are being requested.

Various data stores may be included in assessment network 100. The data stores may include, for example, an account data store 176, which may include login credentials for one or more users or clients and/or types of data access to be granted to each user or client; a process data store 177, which may identify facility analysis characteristics pertaining to particular data elements (e.g., identifying a facility, piece of equipment, and/or processing time); data sets store 178, which may identify one or more data sets associated with a given client or material, such as a sample; and one or more data-set expressions or signatures associated with a given client or material, such as a sample. The data stores may further or alternatively include a results data store 181, which may identify one or more sparse indicators identified by and/or one or more results generated by assessment system 105 that are associated with a given client or material, such as a sample.

The data stores may further or alternatively include a reports data store 182, which may include one or more report templates (e.g., each associated with one or more result types) and/or one or more reports to be transmitted or having been transmitted to a client device; and/or a relevance support data store 183, which may identify which types of data (e.g., data-set units, full or partial reference data sets, activity patterns, inputs, records, tests, etc.) are established to be, potentially, established not to be, or unknown whether to be relevant for evaluating a particular type of likelihood (e.g., a likelihood of transitioning into a particular state).

Relevance support data store 183 may include identifications of one or more content objects. The identifications may include, for example, web addresses, journal citations, or article identifiers. In some instances, an identification identifies one or more sources associated with the content object (e.g., scientist, author, journal, or data store). Content objects may be tagged with one or more tags, which may identify, for example, a sparse indicator, a data-set unit, a data set, and/or a type of assessment. In some instances, each of one or more content objects are associated with a score which may reflect a credibility of the content object. The score may be based, for example, on a publication frequency of a source, an impact factor of a source, a date of publication of the content object, and/or a number of citations to the content object.

Assessment network 100 may also include a user device 180 configured to detect input from a user 185. User 185 may be associated with an account or other authentication data indicating that access to some or all of the data is to be granted. Accordingly, user 185 may be able to interact with various interfaces (presented at user device 180) to view data pertaining to one or more particular clients (e.g., in an identified or de-identified manner), to view summary data that relates to data from multiple clients, to explore relationships between data types, and so on. In some instances, an interface may be configured to accept inputs from a user 185 so as to enable the user to request data pertaining to (for example) materials with sparse indicators in particular dataset units, particular sparse indicators and/or state likelihoods.

In some embodiments, the assessment system 105 may be involved in the generation of a report. The assessment system 105 may then send the report to client 125 or external facility 120, such as by way of client device 130 or requestor device 110a. In some embodiments, the assessment system 105 may be involved in the generation of a communication or report that may identify an anomaly subset of iteration data that has been determined by the assessment system 105. The assessment system 105 may then send this communication out to various components within the assessment network 100, such as facility 120, data generator 140, and external assessment device 190 used by the developer 195, in order to make the data processing workflow more accurate and efficient. Additional information about this communication is provided in regards to FIG. 5.

Genetic assessment network 100 can also include an external assessment device 190 configured to detect input from a developer 195. Via such inputs, external assessment device 190 may send electronic requests for genetic and/or other data (e.g., relating to particular genes, a particular client and/or particular client inputs) to assessment system 105. Assessment system 105 may evaluate the request to determine, for example, whether a corresponding client 125 authorized such access (which may be verified via a communication exchange between assessment system 105 and client device 130) and/or whether such access is relevant to a purported type of analysis. If the evaluation indicates that access is to be granted, assessment system 105 may (for example) send an instruction communication to data generator 140 to conduct a new analysis of an existing sample, send a data request to a device (e.g., access control device 160b, client device 130) and/or retrieve data from a data store (e.g., and extract pertinent information from any larger data structure, such as extracting gene-specific data from a genome). Provision of such data may be conditioned upon or may require payment (e.g., by a client or developer) of a fee.

Workflows

This disclosure makes frequent reference to workflows. As previously discussed, the processing of data may involve multiple steps, and each step may include a process or task. These tasks may be performed by any entity or device. As referenced herein, a workflow may be broadly associated with a collection of processes or tasks. Additionally, a workflow may include a structure and definition for each of the processes or tasks within the workflow. In general, a workflow may be performed repeatedly, with each iteration of a workflow involving the performance of the tasks defined by the workflow. In some embodiments, each iteration of the workflow may correspond to a given client. For example, in some embodiments, each iteration may correspond to generating a likelihood variable for a given client and may involve various other entities (e.g., reviewers, facilities, etc.), which may be selected based on, for example, user preference, a physical location of a client device, and/or availability.

For the purposes of facilitating understanding, the following non-limiting example of a workflow is described within the context of FIG. 1. Specifically, generating outputs for users and/or requestors may involve multiple steps, each of which may include a process, which may be referred to herein as a task, of an entity and/or device. A workflow may include a structure and definition for these processes. For example, various workflows may include some or all of the following tasks:

Inputs are collected at client device 130, transmitted by client device 130, and received by assessment system 105, where the inputs correspond to a preliminary request to conduct an assessment based on a material and ensure that all required inputs have been received;

A same or different client device 130 (e.g., a wearable device) collects and transmits other data indicative of the client's activity or status;

Inputs collected at requestor device 110a, 110b and transmitted to assessment system 105 that correspond to a request for assessment for the client;

Access control device 160b at facility 120 collects and transmits record data of the client;

Distribution device 135 receives alert corresponding to new request and address information and confirms shipping of kit for sample collection to the client;

Client 125 receives kit, collects material and sends to data generator 140;

Assessment device(s) 145 collects data-set data, and access control device 160a sends facility data to assessment system 105;

Assessment system 105 detects any sparse indicators in data set(s) and/or any modifications in data set expression;

Assessment system 105 assigns any sparse indicators and/or data set availability modifications;

Evaluation device 170 collects inputs identifying an assignment of any sparse indicators and/or data set availability modifications as of an unknown likelihood;

Confirmatory facility testing of any sample associated with a sparse indicator and/or data set availability modification having a particular assignment at same or different facilities;

Assessment system 105 aggregates sparse indicator data, assignment data, record data, user or client inputs, other data, and/or activity or status data and generates one or more likelihood variables;

Assessment system 105 generates electronic report with the one or more likelihood variables;

Evaluation device 170 and/or requestor device 110a collect inputs indicating that the electronic report is approved for transmission to client device 130; and Assessment system 105 transmits the electronic report to client device 130.

In some embodiments, a workflow may include a task order that indicates that, for example, a first task is to be completed prior to performance of a second task, though a workflow may alternatively be configured such that at least some tasks may be performed in parallel. In some embodiments, one or more tasks in a work flow are conditional tasks that need not be performed during each iteration of the work flow. Rather, whether a conditional task is to be performed may depend on a circumstance, such as whether a result from a prior task is of a particular type or exceeds a threshold.

It should be noted that through the use of a workflow, the assessment system 105 may track timing of individual tasks during individual iterations of a work flow. For tasks performed at assessment system 105, timing may be directly determined. For tasks performed by, at, and/or via another device, assessment system 105 may track timing via electronic transmissions between systems. For example, a start may be identified by an instruction communication sent from assessment system 105 and/or a when a communication was received indicating that the corresponding task was beginning. As another example, an end time may be identified by transmission of a communication including a result of the corresponding task sent from assessment system 105 and/or when a communication was received indicating that the corresponding task was complete. From these transmissions, the completion times of individual processes may then be monitored and assessed. By monitoring the completion times of individual processes, machine-learning and big-data analysis can be applied in order to identify individual processes that are taking a long time to complete. This information can then be used to improve the efficiency of those specific processes and optimize the overall workflow. The use of machine-learning to identify anomaly subsets in this manner is further described in regards to FIG. 5.

In connection with the performance of workflows is a collection of data, referred to herein as iteration data, which may contain data associated with many iterations of the workflow. In some embodiments, the iteration data may include genomic data (e.g., sequences), genetic-analysis result data, user data (e.g., provided via user input), and/or sales data (e.g., who ordered a test, whether a promotion was used, a sales date). In some embodiments, this iteration data may include workflow processing time periods or processing times of tasks within the workflow for individual iterations of the workflow. In some embodiments, this iteration data may include data identifying laboratories, devices, time periods, and geographies associated with individual iterations of the workflow. However, it should be noted that the term iteration data may refer to an abstract collection of data. In some embodiments, the iteration data may have a well-defined data structure and may be stored across one or more data stores. In other embodiments, iteration data can be a reference to many types of data that can be stored across numerous data stores and data sources that the assessment system 105 may query, receive, and use as needed. A visualization of iteration data and an example structure is provided in FIG. 3 and its accompanying description.

Processing of Sparse Indicators

In some embodiments, the workflow for analyzing genetic data may include processes or tasks directed at the detection and identification of sparse indicators. An overview of the detection and identification of sparse indicators is provided below. Additional detail on this topic can be found in U.S. Non-Provisional patent application Ser. No. 15/163,191, titled "UNIT-SPECIFIC DATA REPOSITORY QUERIES FOR RESTRICTED PROCESSING OF EXTERNAL ASSESSMENT SYSTEM REQUESTS", filed May 24, 2016, which was previously incorporated by reference herein.

For an iteration of the workflow, one or more sparse indicators can be determined by comparing generated data (e.g., a client data set including a client's sequenced genome) against reference data (e.g., a reference genome). This may involve aligning a portion of the generated data to a portion of the reference data, such that individual values of the generated data can be compared to corresponding values in the reference data. Differences between the generated data and the reference data correspond to sparse indicators associated with the generated data set for the particular client.

In some embodiments, the generated data may be generated using a set of reads that have been aligned to a certain position, and the set of reads may be obtained from using a laboratory or device to read portions of a client's genetic material. In some embodiments, the generated data may include a client data set. The client data set for a particular client may include an identifier data set (e.g., a sequence) that identifies a base at each of a set of positions, such at each position along one or more data-set units (e.g., genes). The identifier data set may be generated by, for example, identifying a set of identifiers as those present in the reads aligned to a given position, at the position, and detecting a most common identifier from amongst the set of identifiers.

Different types of sparse indicators (e.g., variants) may be identified this way, such as a one-element sparse indicator representing a single data element different from a reference data set, or a structural sparse indicator representing a set of consecutive data elements different from a reference data set (e.g., a structural variant). A structural sparse indicator may be detected upon determining (for example) that a series of elements in a data set generally differ from those in a reference data set or that values in a coverage set change across the set so as to indicate that a portion of the reference data set is over- or underrepresented in the data set.

After the sparse indicators are identified, the workflow may further involve the system classifying each sparse indicator or assigning it to a data bucket. Each sparse indicator may be assigned to a bucket which may reflect a predicted impact of the detected difference. In some instances, a set of buckets are defined. Each of one, more or all of the buckets may correspond to a predicted likelihood that a client will progress to a given state. A state may include, for example, utilizing a full memory bank, a condition (e.g., cancer), reduced bandwidth, and/or a connection drop. Thus, buckets may reflect whether and/or a degree to which a difference causes the state (e.g., reflecting memory requirements, whether the difference is (e.g., and/or is likely to be) pathogenic or benign), consumes bandwidth, and/or impairs a connection's stability). For each client, a determination as to how many sparse indicators were assigned to one or more particular buckets may be used to generate a result that identifies a state-progression prediction.

The assignment of individual sparse indicators to various data buckets may be performed in various ways. For example, the system may reference a look-up table may include a set of entries, each of which corresponds to a sparse indicator. The system may reference the table using a position and identifier for each sparse indicator, or by a range of positions and type of sparse identifier (e.g., type of structural sparse identifier and/or one or more corresponding position ranges in a reference data set). The look-up table may then inform the system of the classification or bucket assignment listed for each sparse indicator. Furthermore, the table may also include a confidence associated with such an assignment. For instance, from observations over time it may be determined that a specific sparse indicator at a specific location should be associated with a certain assignment at a 99% confidence. Thus, in order to classify various sparse indicators, the system may need access to information regarding types, identities, values, assignments, and/or confidence metrics associated with various sparse indicators that can be identified from the generated data. This information may also be used to determine classifications or bucket assignments for various types of sparse indicators (e.g., structural sparse indicators), such as a sparse indicator that indicates that elements from Position X to Position Y are not present in a client data set. In some embodiments, the classification may involve determining whether each of the sparse indicators is a deviation that is pathogenic in nature (e.g., that particular difference between the client data set and the reference data set may lead to increased probabilities of certain diseases arising). In some embodiments, a machine-learning model can be trained in order to classify and assign sparse indicators to various data buckets. The machine-learning model may then be applied to individual sparse indicators in order to evaluate the types, identities, and values of those sparse indicators and assign them into a data bucket. The model may also be able to determine any confidence levels associated with the prediction or the existence of those sparse indicators.

However, in some cases, additional validation needs to be performed on sparse indicators identified by the system. There may be various reasons behind requiring validation, which include the identification of unlikely sparse indicators, or incorrect and unlikely data bucket assignments for a sparse indicator. Machine-learning techniques and big-data analysis can be used to identify sparse indicators that need additional validation, as well as the reasons behind requesting that additional validation. Based on the reasons for validation, the system may then take the appropriate action for validating those sparse indicators (e.g., the client's genome may be sequenced again with more expensive and more accurate sequencing). The use of machine-learning to identify anomaly subsets in this manner is further described in regards to FIG. 5.

Figure 2:
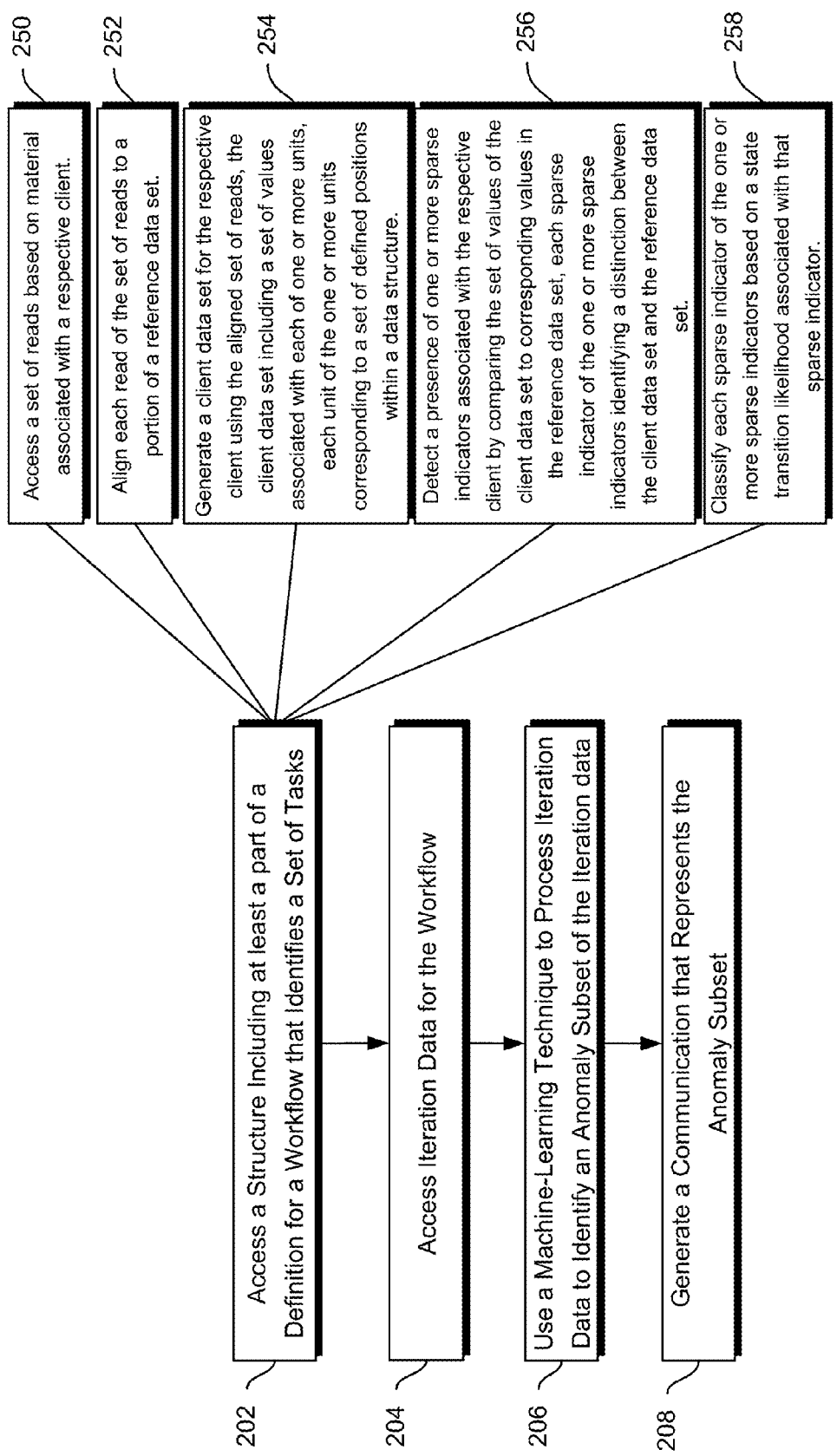
FIG. 2 illustrates a flow chart for data processing, in accordance with some embodiments.

Data Processing—FIG. 2

In reference back to the figures, FIG. 2 shows a flow chart for the data processing. More specifically, the figure illustrates how machine learning techniques may be used to identify an anomalous subset of iteration data for a workflow identifying a set of tasks for processing and analyzing genetic data.

At block 202, the system, such as an assessment system 105, may access a data structure that includes at least part of a definition for a workflow that identifies a set of tasks, which may include one or more orders indicating that the tasks are to be performed—at least in part—sequentially and/or identifying tasks that may be performed in parallel. The workflow can, in some instances, identify one or more conditions for performing at least one task, which may include a condition based on a result from a previous task.

A workflow can be defined, for example, at least in part by a user, developer or machine-learning algorithm. In some instances, multiple workflows are defined, and each workflow may be associated with, for example, one or more different conditions, time periods and/or developers. An accessed workflow can include one that is identified as pertaining to a particular user or user device and/or condition.

Each of one, more or all of the tasks within the set of tasks may include any task, process, or step carried out by one or more components of the assessment network 100 illustrated in FIG. 1. In some instances, each task in the set of tasks is to be performed by assessment system. In some instances, one or more tasks may be performed by the assessment system 105. The figure shown illustrates a set of example tasks within block 250, block 252, block 254, block 256, and block 258. These example tasks are provided for the purposes of facilitating understanding of the data processing being performed and are not meant to be limiting.

For example, block 250 describes a work flow task involving accessing a set of reads based on material associated with a respective client. In some embodiments, the set of reads may be data generated by one or more devices associated with the data generator 140 (such as an asssessment device 145 or technician device 150). The set of reads may have been generated based on material associated with a client, such as a sample of material provided by the client 125. Each of the set of the set of reads may thus correspond to a single client. Each read of the set of reads may include an ordered set of identifiers, which may have been identified at data generator 140 based on a client sample. At least some of the set of reads may vary with regard to length.

Accessing the set of reads may include receiving the set of reads (e.g., from data generator 140) or retrieving the set of reads from a local or remote storage. Each data read in a set of reads may correspond to a same client, or at least some of the plurality of data reads may correspond to different clients. In various instances, the set of reads may be transmitted to assessment system 105 in a batch-mode, in a streaming mode, in real-time as data is produced, and/or upon request. The data may be initially stored at a data store local or remote to data generator 140. A given transmission or stream may include data that corresponds to a single, or in other instances to multiple, client, sample, and/or data reads. In some instances, access control device 160a evaluates one or more transmission conditions, which may indicate, for example, whether and/or what data is to be transmitted given a quantity of data collected (e.g., generally, since a past transmission and/or for a given client or sample) and/or given a time since a previous transmission. In one instance, as data reads are generated by an assessment device, a data set is generated so as to include each new data read and one or more identifiers (e.g., of a client, sample, time and/or facility device). The data may then be transmitted via a discrete communication (e.g., via FTP, over a webpage upload, email message, or SMS message) to assessment system 105. In one instance, the data may then be appended to a stream that is being fed to assessment system 105.

Block 252 describes an example work flow task involving aligning each read of the set of reads to a portion of a reference data set. In some embodiments, the assessment system 105 may process the set of reads by, for example, aligning individual reads to a reference data set for the purposes of generating a client data set for the client associated with the set of reads.

Block 254 describes an example work flow task involving generating the client data set for that client using the aligned set of reads. In some embodiments, the client data set may include a set of values associated with each of one or more units, each unit of the one or more units corresponding to a set of defined positions within a data structure. For example, a client data set for a particular client may include an identifier data set (e.g., a sequence) that identifies a base at each of a set of positions, such at each position along one or more data-set units (e.g., genes). The identifier data set may be generated by, for example, identifying a set of identifiers as those present in the reads aligned to a given position and detecting a most common identifier from amongst the set of identifiers. As another example, a client data set for a particular client may include a coverage data set that identifies, for each position of a set of positions (e.g., at each position along one or more data-set units) a number of reads aligned to overlap with the position.

Block 256 describes an example work flow task involving detecting a presence of one ore more sparse indicators associated with the respective client by comparing the set of values of the client data set to corresponding values in a reference data set. In some embodiments, each sparse indicator may identify a distinction between the client data set and the reference data set. In some embodiments, the assessment system 105 may be tasked with detecting these differences between the data sets. For example, a difference may be identified by detecting a difference, at a given position, between a value of the identifier data set and a corresponding value of the reference data set. As another example, a difference may be identified by detecting an abrupt change in a coverage data set (e.g., such that values abruptly change approximately 2- or 3-fold). A sparse indicator may be defined for each difference so as to identify a type of difference observed (e.g., what identifier was present in an identifier data set as opposed to a reference data set or how a coverage data set changed) and a position (e.g., with respect to the reference data set and/or along one or more data-set units) at which the difference was observed.

Block 258 describes an example work flow task involving classifying each sparse indicator of the one or more sparse indicators that have been detected (e.g., from the task performed at block 256). Each sparse indicator may be assigned to a bucket which may reflect a predicted impact of the detected difference. In some instances, a set of buckets are defined. Each of one, more or all of the buckets may correspond to a predicted likelihood that a client will progress to a given state. A state may include, for example, utilizing a full memory bank, a condition (e.g., cancer), reduced bandwidth, and/or a connection drop. Thus, buckets may reflect whether and/or a degree to which a difference causes the state (e.g., reflecting memory requirements, whether the difference is (e.g., and/or is likely to be) pathogenic or benign), consumes bandwidth, and/or impairs a connection's stability). For each client, a determination as to how many sparse indicators were assigned to one or more particular buckets may be used to generate a result that identifies a state-progression prediction. The result may be transmitted to a requestor device 110 and/or client device 130.

Turning back to the primary flow illustrated in FIG. 2, at block 204 the system may access iteration data for a workflow, such as the ones previously described. The interation data may contain data for one or more clients. For each client, the iteration data may have data associated with a single iteration of a workflow (e.g., corresponding to a particular set of reads) pertaining to that client. This data may include data items specific to corresponding iterations of the workflow, such as an identifier of that iteration, an identifier of where that iteration of the workflow originated from, a time at which the iteration of the workflow was performed, and so forth. The data may also include data items that were used, generated, or analyzed within the various tasks performed during an iteration of the workflow. In some embodiments, there may be data items pertaining to a computational characteristic corresponding to performance of each of one or more tasks of a workflow for each of one or more iterations. For example, processing time, memory usage, or CPU usage may be assessed. In some of such embodiments, there may also be a client data set and one or more sparse indicators that are generated or identified by a workflow iteration. A better visualization of the types of data items within the iteration data and the overall data structure for the iteration data can be seen in FIG. 3.

At block 206, the system may use a machine-learning technique to process the accessed iteration data to identify an anomaly subset of the iteration data. Additional details regarding how an assessment system 105 may use machine-learning to identify different anomaly subsets of iteration data is provided in regards to FIG. 5.

At block 208, once the system has identified an anomaly subset of the iteration data, the system may generate a communication that identifies or represents the anomaly subset. Additional details regarding how an assessment system 105 may generated different communications for identifying different anomaly subsets of iteration data is provided in regards to FIG. 5.

Figure 3:
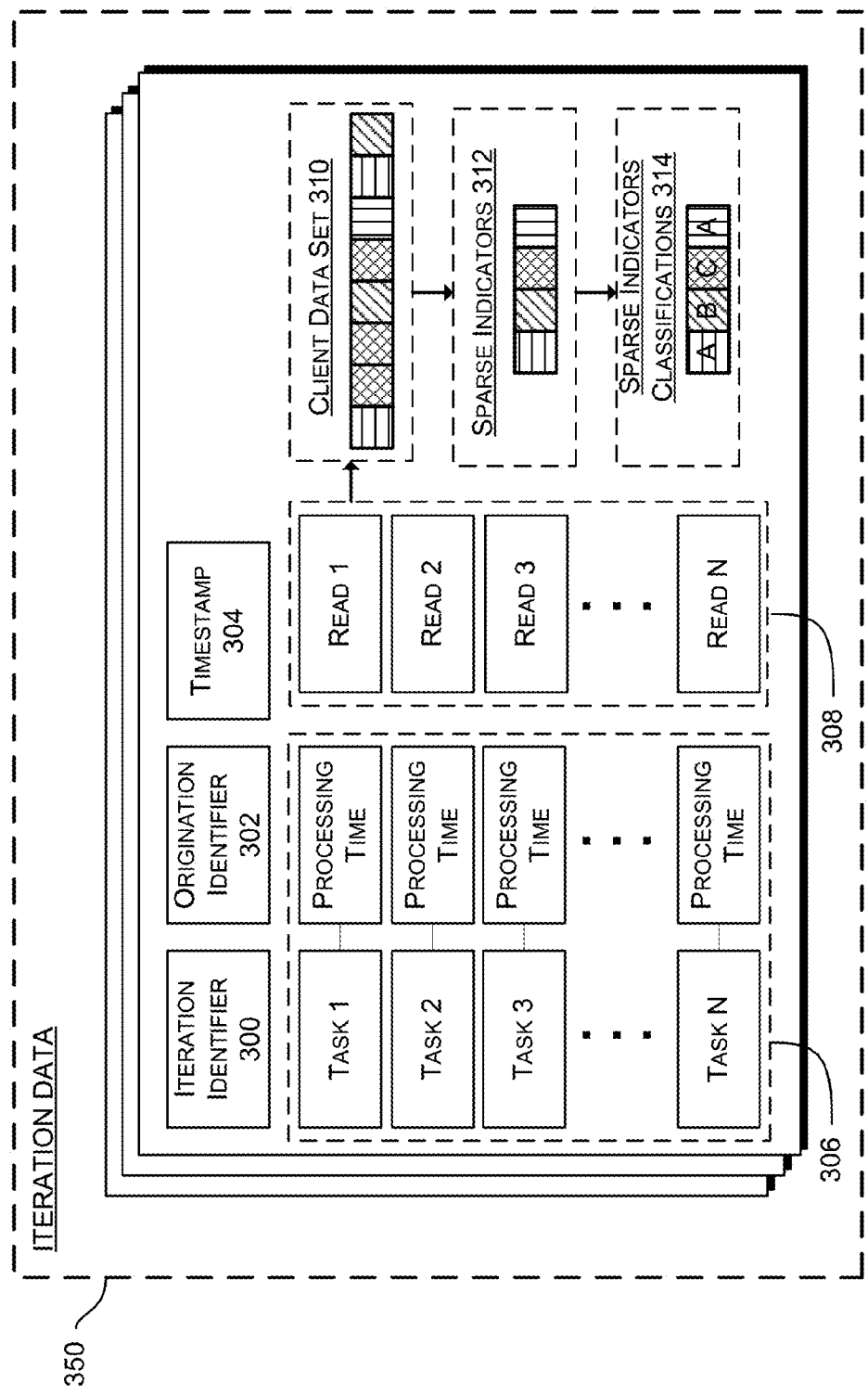
FIG. 3 illustrates example data structures for data used in the data processing, in accordance with some embodiments.
Figure 4:
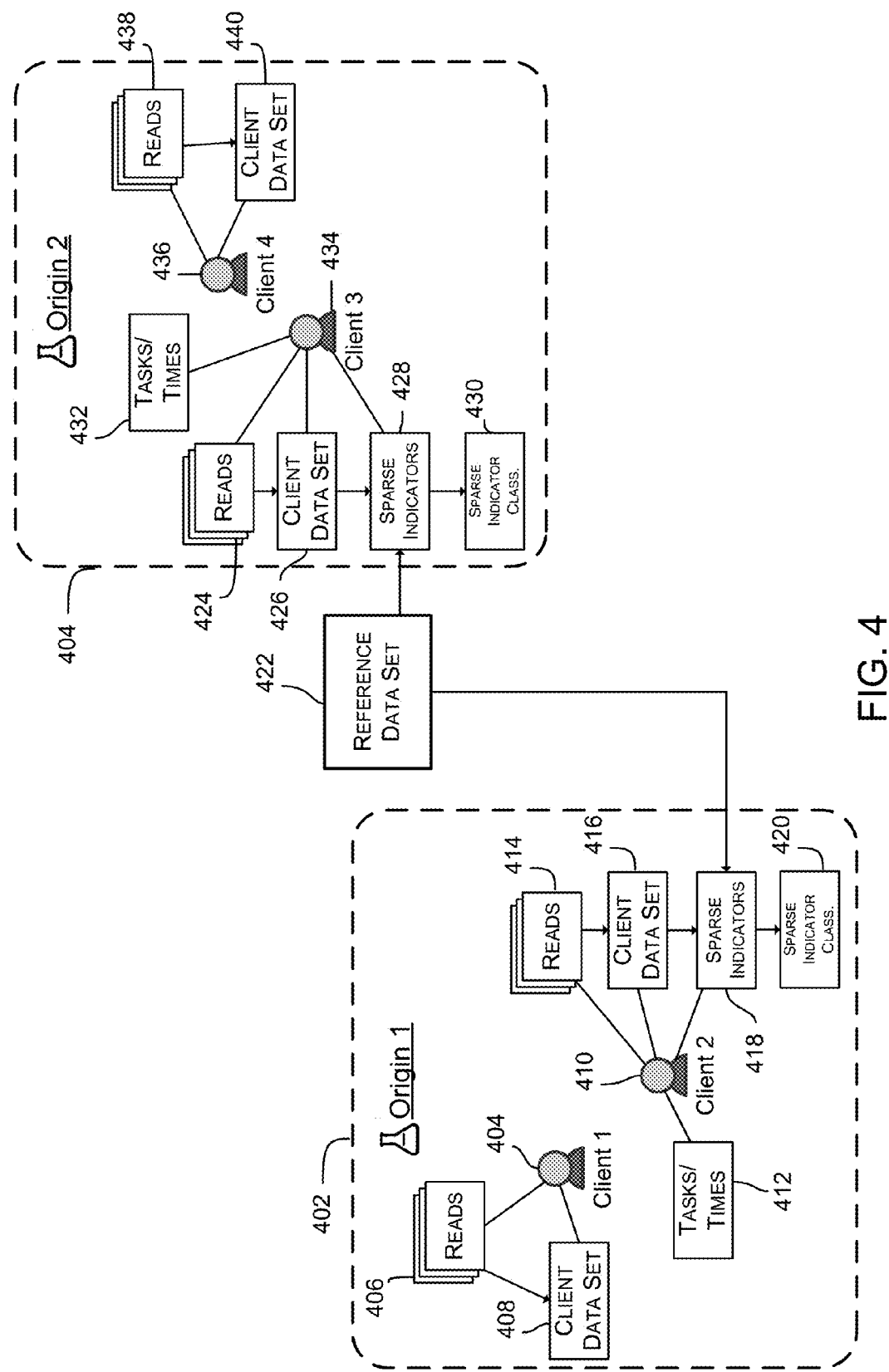
FIG. 4 illustrates example relationships between some of the data used in the data processing, in accordance with some embodiments.

Iteration Data—FIGS. 3 & 4

FIG. 3 illustrates example data structures for data used in data processing workflows, in accordance with some embodiments. More specifically, FIG. 3 illustrates iteration data 350 that may be used in the data processing and an example structure for that data. It is appreciated that the iteration data 350 need not include each depicted data type and/or may include other non-depicted data types.

In some embodiments, the iteration data 350 may include data pertaining to a plurality of iterations of a workflow, such as the workflow referred to in the flowchart of FIG. 2 which is associated with a step of tasks. In some of such embodiments, each iteration of a workflow may be associated with a single client. In some of such embodiments, a particular client may be associated with more than one iteration of the workflow—such as if that particular client has provided numerous samples of material and requested the workflow to be performed multiple times. Accordingly, in some embodiments, the iteration data 350 may collectively include data for many iterations of the workflow that were performed for many clients, with each iteration being associated with a specific client.

In some embodiments, a single iteration of a workflow may be associated with an iteration identifier 300. In some of such embodiments, the iteration identifier 300 may be unique for each single iteration of a workflow and allow the assessment system 105 to identify that specific workflow iteration and/or the client that iteration is associated with. For example, the iteration identifier 300 may be used to identify a specific client device 130 and/or client 125 that provided material for the workflow.

In some embodiments, a single iteration of a workflow may also be associated with an origination identifier 302. In some embodiments, the origination identifier 302 may identify where certain data associated with that iteration originated from. For example, the origination identifier 302 may identify a specific laboratory (such as external facility 120 or data generator 140) that data originated from or a specific device (such as assessment device 145 or technician device 150) that data was generated using. In some embodiments, the origination identifier 302 may instead identify a source that requested that iteration of the workflow be performed (such as a requestor device 110 or a requestor 115). In some embodiments, the origination identifier 302 may instead identify the client that specific iteration is associated with, such as the client device 130 or the client 125.

In some embodiments, the origination identifier 302 can include one or more data-source variables, which may identify or characterize a data generator and/or client. A data-source variable may be used to identify the source of a set of data within the iteration data. For example, a data-source variable can be associated with a set of aligned reads generated by a specific data source. This data-source variable preserves any relationships between sets of reads for different iterations, as well as any consistencies across those sets of reads. For example, an iteration of the workflow may be performed for a first client to obtain a set of reads from "Device A". A different iteration of the workflow may be performed for a second client to obtain a set of reads, also from "Device A". Thus, the data-source variable identifying "Device A" can be associated with both sets of reads. Thus, if the set of reads for the first client and the set of reads for the second client both contain errors, the system can determine that both faulty sets of reads originated from "Device A" and infer that "Device A" is the source of the error. Furthermore, the system could query the iteration data using the data-source variable to determine every set of reads that originated from "Device A", as well as data for the iterations associated with those sets of reads, in order to identify the anomaly subset. For example, the system could query the iteration data to find all sets of reads from "Device A", which may include a set of reads in an iteration for a third client. The set of reads for that third client may also be part of the identified anomaly subset. Furthermore, the system could look at data for that iteration for the third client, such as the processing times for the various tasks performed in that iteration, and use that information as additional datapoints for deducing the issue with "Device A".

In some embodiments, a single iteration of a workflow may also be associated with a timestamp 304. In some embodiments, the timestamp 304 may identify a time associated with that iteration of the workflow. For example, the timestamp 304 may identify a time at which that iteration of the workflow was initiated. This timestamp 304 may be helpful in diagnosing errors in the workflow or determining how to better improve and optimize the workflow. For instance, the assessment system 105 may determine that data for workflow iterations originating out of "Facility A" between the times of 9:00 AM to 10:00 AM on a certain day contain numerous errors as a result of power issues experienced at Facility A. Thus, combinations of the iteration identifier 300, the origination identifier 302, and/or the timestamp 304 may be helpful in identifying and locating specific sets of data. In some embodiments, the information contained in the iteration identifier 300, the origination identifier 302, and/or the timestamp 304 may be contained in a single identifier. Thus, each iteration can correspond to a single client but may be selected based on numerous other criteria, such as entities (e.g., physicians, reviewers, laboratories, etc.) involved in the generation of that iteration's data, client preferences, a geographical location of a client device, when the iteration was initiated, and so forth.

In some embodiments, a single iteration of the workflow may be associated with a set of processing times 306 corresponding to the set of tasks defined by the workflow. For example, if a workflow is defined by a total of five tasks, the set of processing times 306 for a single iteration of the workflow may contain a value corresponding to each of the five tasks pertaining to the amount of processing time that was used to complete that specific task. Accordingly, each processing time in the set of processing times 306 may be associated with a task performed in that workflow iteration; the processing times in the set of processing times 306 may be particularly useful when the task corresponding to each processing time can be determined.

However, in various embodiments, any other computation resources can be used instead of—or in addition to—processing times 306 as a metric. For example, CPU load or usage, memory load or usage, hard drive load or usage, and/or network usage can be monitored for various tasks within the workflow. Accordingly, machine-learning can be similarly applied to identify tasks in the workflow that are overutilizing any kind of computational resource. For instance, it may be advantageous to identify an anomaly subset of tasks within the workflow that are overutilizing the harddrive. Since accessing data on a hard drive can, in some cases, be much slower than accessing data stored within memory, there are efficiency gains that can be obtained by adding memory capacity so the harddrive is no longer overutilized by those tasks.

It should also be noted that iteration data 350 need not contain actual processing times. In some embodiments, the processing times 306 may be information that is abstracted from other data. For example, the assessment system 105 may track start and completion times of individual tasks during individual iterations of a workflow. This monitoring can be performed automatically and/or in response to a query communication from user device 180. For tasks performed at assessment system 105, start and completion times can be directly determined. For tasks performed by, at and/or via another device, assessment system 105 may track start and completion times via communications. For example, a start time may be identified as a time at which an instruction communication was sent from assessment system 105 and/or a time at which a communication was received indicating that the corresponding task was beginning. As another example, a completion time may be identified as a time at which a communication including a result of the corresponding task was received at assessment system 105 and/or a time at which a communication was received indicating that the corresponding task was complete. Thus, the assessment system 105 may determine processing times for individual tasks by taking the difference between corresponding task completion and task start times. This may be facilitated by associating task identifiers with corresponding task completion and task start times. In some embodiments, once a task completion time is determined, the assessment system 105 may be configured to automatically update the iteration data 350 with a processing time associated with an identifier of that particular task. The identifier of the task may be selected based on, for example, which task was pending in a workflow iteration for a request, a task identified in the incoming communication and/or a type of device having transmitted the detected communication.

In some embodiments, a single iteration of the workflow may be associated with a set of reads 308. These reads may be generated using material received from the client associated with that workflow iteration. As previously described, a data generator 140 may include one or more assessment devices 145 and/or technician devices 150 for the generation of data reads based on the material.

In some embodiments, a single iteration of the workflow may include an associated client data set 310 that may have been generated using the set of reads 308 through the methods previously described. The illustrations for both the client data set 310 and the sparse indicators 312 shown in the illustration mirrors those shown in FIG. 8 of U.S. patent application Ser. No. 15/163,191, filed May 24, 2016, and previously incorporated by reference. Consulting that figure and the corresponding description for that figure may assist in understanding how the client data set 310 and the sparse indicators 312 fit into the overall workflow.

In some embodiments, a single iteration of the workflow may be associated a set of sparse indicators 312 generated using the client data set 310 and a reference data set through the methods previously described. As a non-limiting example, each sparse indicator may be determined by comparing the set of values of the client data set 310 and the reference data set. Each sparse indicator of the set of sparse indicators 312 may identify a distinction between the client data set 310 and the reference data set.

In some embodiments, a single iteration of the workflow may be associated a set of sparse indicator classifications 314 generated using the sparse indicators 312 through the methods previously described. As a non-limiting example, each sparse indicator may be identified and assigned to a data bucket or classification.

FIG. 4 illustrates example relationships between some of the data used in the data processing, in accordance with some embodiments. More specifically, FIG. 4 provides additional context on the types of data items in the iteration data available for different iterations of the workflow.

For instance, the figure shows a first origin 402 and a second origin 404, which may represent different facilities, laboratories, or devices from which data pertaining to the clients originates. For example, the first origin 402 could be a data generator 140 that produced data for a first client 404 as well as a second client 410, such as by generating a set of reads from material supplied by those clients. In some embodiments, the data for the workflow iteration associated with each of those clients may have an identifier, such as an iteration identifier 300 or an origination identifier 302, which can be used to determine that the data for those two clients came from the first origin 402.

For instance, the figure shows a first origin 402 and a second origin 404, which may represent different facilities, laboratories, or devices from which data pertaining to the clients originates. For example, the first origin 402 could be a data generator 140 that produced data for a first client 404 as well as a second client 410, such as by generating a set of reads from material supplied by those clients. In some embodiments, the data for the workflow iteration associated with each of those clients may have an identifier, such as an iteration identifier 300 or an origination identifier 302, which can be used to determine that the data for those two clients came from the first origin 402. Likewise, the second origin 404 is seen as the originator for a third client 434 and a fourth client 436.

The first client 404 is shown as being associated with a set of reads 406 generated from material supplied by that client. The set of reads 406 can be used in generating the client data set 408 associated with the first client 404. The second client 410 is also shown as being associated with a set of reads 414 generated from material supplied by that client. The set of reads 414 can be used in generating a client data set 416 associated with the second client 410. That client data set 416 can be used, along with a reference data set 422, to determine a set of sparse indicators 418 associated with the second client 410. Those sparse indicators 418 can be properly identified and classified in order to determine the sparse indicator classifications 420 associated with the second client 410. In this example figure, the first client 404 is not shown as being associated with a set of sparse indicators or their classifications—presumably because the iteration of the workflow for the first client 404 has not progressed to the point where those data items would be generated. In contrast, the workflow for the second client 410 has resulted in the generation of the sparse indicators 418 and the sparse indicator classifications 420, so the second client 410 is associated with a set of processing times 412 corresponding to each of the tasks performed in the workflow iteration for the second client 410.

Similarly, the fourth client 436 is also shown as being associated with a set of reads 438 generated from material supplied by that client. The set of reads 438 can be used in generating the client data set 440 associated with the fourth client 436. The third client 434 is also shown as being associated with a set of reads 424 generated from material supplied by that client. The set of reads 424 can be used in generating a client data set 426 associated with the third client 434. That client data set 426 can be used, along with t reference data set 422, to determine a set of sparse indicators 428 associated with the third client 434. Those sparse indicators 428 can be properly identified and classified in order to determine the sparse indicator classifications 430 associated with the third client 434. In this example figure, the fourth client 436 is not shown as being associated with a set of sparse indicators or their classifications—presumably because the iteration of the workflow for the fourth client 436 has not progressed to the point where those data items would be generated. In contrast, the workflow for the third client 434 has resulted in the generation of the sparse indicators 428 and the sparse indicator classifications 430, so the third client 434 is now associated with a set of processing times 432 corresponding to each of the tasks performed in the workflow iteration for the third client 434. The types of data items available in regards to each client and/or single iteration of the workflow can be better visualized by referencing this figure with FIG. 3 and its corresponding description.

In this illustrated example, the accuracy of the set of reads 406 from the first client 404 and the set of reads 414 from the second client 410 (and any data generated from those sets of reads) may be a reflection of the accuracy and instrumentation capabilities of the first origin 402 in generating data. At the same time, the accuracy of the set of reads 424 from the third client 434 and the set of reads 438 from the fourth client 436 (and any data generated from those sets of reads) may be a reflection of the accuracy and instrumentation capabilities of the second origin 404 in generating data. Thus, in some embodiments the assessment system 105 can compare data originating from the first origin 402 to data originating from the second origin 404 to determine any statistical differences between the data which can be used to identify any inaccuracies or instrumentation errors associated with any of the data origins. This information can be provided in a communication to notify that one of the data origins is associated with errors (and should be fixed), or the assessment system 105 may be able to correct some of those statistical differences automatically. Additional information about the types of statistical differences that can be determined, how they can be determined, and how they can be corrected is provided in regards to FIG. 5.

Also as shown in the illustrated example, both the second client 410 and the third client 434 are each associated with a set of processing times, a set of sparse indicators, and a set of determined sparse indicator classifications. For any iterations of the workflow that have an available set of processing times, those processing times can be used to determine whether the task corresponding to each processing time took an abnormal amount of time. By identifying any tasks taking an abnormal amount of time, any systemic inefficiencies associated with the first origin 402, the second origin 404, or the method of performing that task itself can be identified in order to allow for future optimization of the workflow.

For any iterations of the workflow that have an available set of sparse indicators and/or sparse indicator classifications, the assessment system 105 can determine if the identification of any of those sparse indicator classifications proceeded normally or abnormally. An abormally identified sparse indicator classification, for example, may be associated with a higher degree of error in the accuracy of that sparse indicator classificaton. Based on that information, the assessment system 105 may further determine whether to double-check the accuracy of that sparse indicator classification. Since double-checking the accuracy of a sparse indicator classification takes time to perform, the selective determination of whether to double-check the accuracy of a sparse indicator classification can optimize the workflow and reduce the time needed to perform an entire iteration of the workflow.

Figure 5:
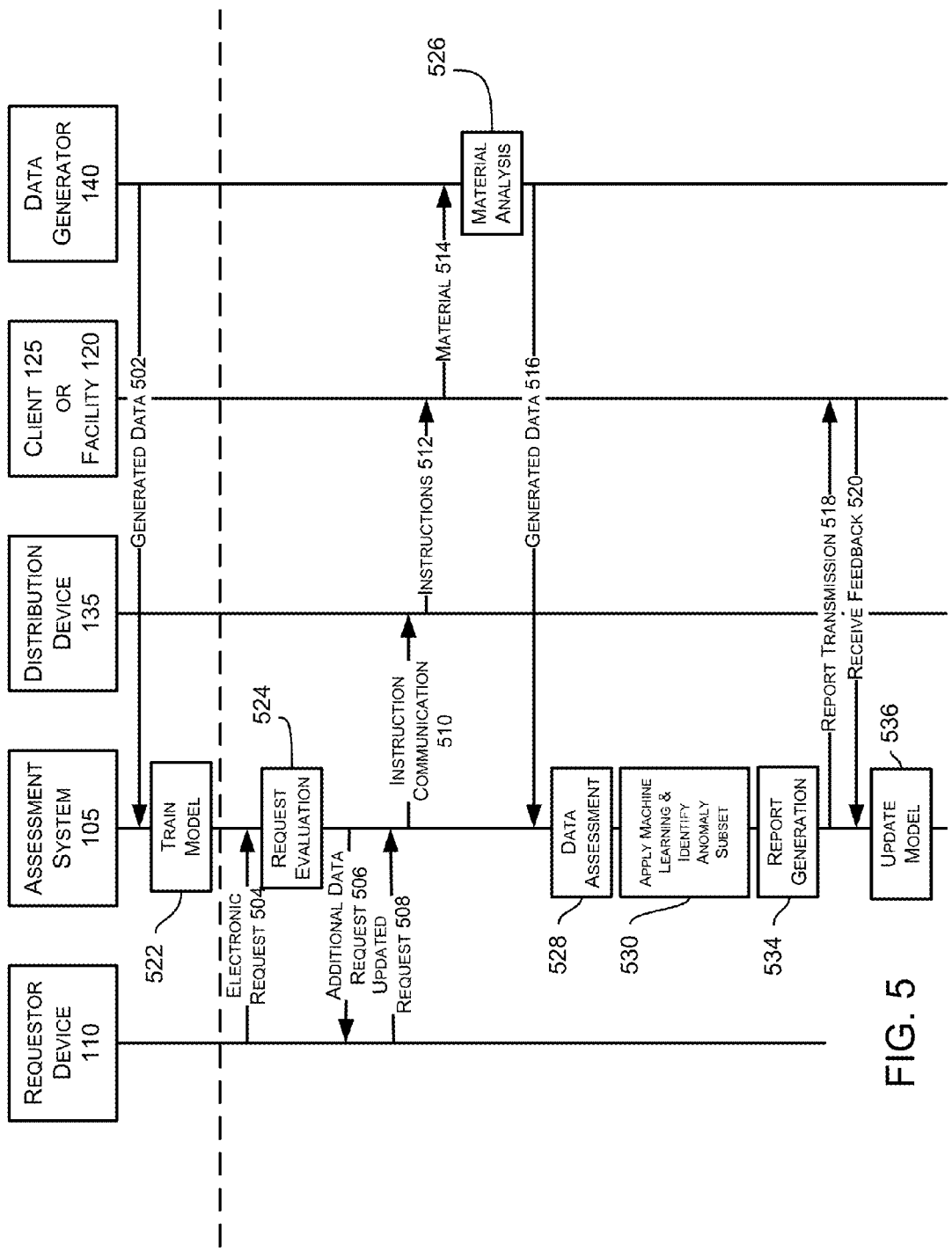
FIG. 5 shows a communication exchange between systems and devices of a data processing network, in accordance with some embodiments.

Communication Exchange and Identification of Anomaly Subsets—FIG. 5

FIG. 5 shows a communication exchange between systems and devices of a data processing network, in accordance with some embodiments. This figure provides a simplified example communications flow between some of the components shown in FIG. 1. In practice, any device or component of FIG. 1 may perform additional actions and/or communications at an point within the illustrated communication exchange as described in regards to FIG. 1.

In some embodiments, one or more data generators 140 may first supply a set of generated data 502 to an assessment system 105. The generated data 502 may be a component of iteration data and contain data items generated by the one or more data generators 140. In some embodiments, the generated data 502 may be utilized by the assessment system 105 to perform data processing—including generating client data sets, identifying sparse indicators, and classifying sparse indicators if those steps have not been performed on the data items within the generated data 502. In some embodiments, at block 522, the assessment system 105 may use the generated data 502 and/or data items associated with client data sets, and identified or classified sparse indicators to train a machine-learning model to be able to identify, classify, or predict anomaly subsets of iteration data.

It should be noted that theses steps involving the receipt of the generated data 502 and the training of the model by the assessment system 105 are optional depending on the specific machine-learning technique used. These steps may be optional if assessment system 105 is configured to apply a machine-learning technique involving unsupervised learning. In contrast, these steps may be more useful if the assessment system 105 is configured to apply machine-learning techniques involving supervised learning, which involves inferring a function from a set of training data. Examples of such machine-learning techniques include regression, support vector machines, random forests, ensembles, naïve bayes classifiers, kernel estimators, decision tree learning, case-based reasoning, backpropagation, nearest neighbor methods, artificial neural networks, and so forth. The generated data 502 can be used for input-output pairs to teach and train a predictive model to be later applied to another set of iteration data. For example, the generated data 502 may include sets of processing times corresponding to tasks performed in various iterations of the workflow along with an indication of whether each task was processed in a normal or anomalous amount of time. The assessment system 105 may then take the generated data 502 in order to train a model that can be used to classify whether a task took a normal or anomalous amount of time based on that task's processing time and any other input variables determined to be important.

Moving on, a requestor device 110 may send an electronic request 504 to the assessment system 105. At block 524, the assessment system 105 may evaluate the received electronic request 504. For example, the electronic request 504 may include instructions to conduct a data-set analysis. If the electronic request 504 has been encrypted, the assessment system 105 may decrypt the electronic request 504 in order to evaluate it. In some embodiments, the electronic request may identify, or otherwise indicate, one or more states to be evaluated during the analysis and/or during an assessment. In some embodiments, the electronic request may identify a client and/or include additional data pertaining to the client, such as client-identifying data. The assessment system 105 may determine the particular entity identified by the electronic request 504 and ensure that all required data needed for the data-set analysis has been provided, and that all required data pertaining to that entity has been identified.

If the assessment system 105 determines that all required information has not been identified, an additional data request 506 for missing information may be transmitted back to the requestor device 110. In response, an updated electronic request 508 with the updated information may be transmitted back to the assessment system 105. The specific information being transmitted to the assessment system 105 may depend on an analysis requested, whether, and what kind of, new data-generation processing of a material is required for the analysis, a number of data-set units being assessed (e.g., and whether they have been previously assessed), a number and/or type of analyses being requested, a number and/or type of analyses previously requested, a number and/or type of analyses predicted to be requested subsequently, a state for which a progression prediction is being requested, whether a user is granting other entities' access to the client's data or results, whether a user is authorizing additional analyses to be performed on the client's data, and/or whether a user is granting permission to send offers to request user access to results or reports other than those initially being requested.

When all required information has been provided to the assessment system 105, the assessment system 105 may send an instruction communication 510 to a distribution device 135. In some embodiments, this instruction communication 510 is encrypted prior to transmission and decrypted upon receipt. That instruction communication 510 may include, for example, a name and address of the client and, in some instances, an indication as to what is to be provided to the client for collection of a material for subsequent analysis. In some embodiments, this instruction communication 510 sent by the assessment system 105 may identify the type of analysis, type of material, and/or kit associated with collection of the material.

The instruction communication 510 may thus facilitate and/or trigger a physical distribution of instructions 512, which may include a kit or other sample collection materials, to a client 125. The instructions may include, for example, instructions as to how to collect a material, a container for storing the material and/or information pertaining to an instruction or type of analysis to be conducted. Alternatively, the instructions may be provided to a facility, such as the external facility 120 associated with a requestor 115*a*, that may aid client 125 in obtaining the material.

Afterwards, the client 125 or facility 120 provides the material 514 to the data generator 140 in order for material analysis to be performed. At block 526, the data generator 140 (or one or more devices associated with the data generator 140) generates a set of data reads from the material 514.

The data generator 140 then sends generated data 516 to the assessment system 105. The generated data 516 may include a plurality of data reads, data elements, or sets (e.g., each data read in the plurality of data reads corresponding to a same client, or at least some of the plurality of data reads corresponding to different clients). In various instances, the data may be transmitted to the assessment system 105 in a batch-mode, in a streaming mode, in real-time as data is produced, and/or upon request. The data may also be stored at a data store local or remote to the data generator 140. A given transmission or stream may include data that corresponds to a single, or in other instances to multiple, client, sample, and/or data reads. In some embodiments, there may be multiple data generators 140. Thus, the generated data 516 being received at the assessment system 105 may be derived from data produced by different assessment devices and/or data generators 140.

At block 528, the assessment system 105 may assess the received generated data 516, as well as generate any additional data items to be a part of iteration data. For example, the assessment system 105 may determine client data sets, sets of sparse indicators, and classifications for those sparse indicators based on at least the generated data 516 using methods previously described.

At block 530, the assessment system 105 may consider all of the available iteration data and apply a machine learning technique to the iteration data to determine an anomaly subset of that iteration data. If the machine learning technique involves supervised learning, the assessment system 105 may apply the model that was trained at block 522. In some embodiments, the machine learning technique involves unsupervised learning, such that the assessment system 105 is provided with unlabeled data from the iteration data set and must infer a function from it. Examples of unsupervised learning include anomaly detection, clustering and cluster analysis, multivariate analysis, neural networks such as Hebbian learning or generative adversarial networks, expectation-maximization algorithms, blind signal separation techniques, and so forth. In certain scenarios, and depending on the desired anomaly subset of iteration data to be identified, certain machine-learning approaches are preferable to others.

For example, if the system is configured to determine different statistical results for two different data origin/ sources, unsupervised learning can be used to directly compare data from the two data sources in order to determine whether there is indeed a statistical difference, and the degree of it. However, data from both data sources may actually be erroneous, and unsupervised learning would not be useful to arrive at that conclusion. In comparison, supervised learning could be used to provide a baseline of perfect accuracy to compare data from both data sources against, allowing for a determination that the two different data sources are both producing inaccurate results. In general, the use of unsupervised learning techniques can be useful for discovering inherent groupings or classifications in the data, or for discovering latent rules or variables that govern large portions of the data. In contrast, the use of supervised learning techniques may be better suited for situations where learning-by-example is desired to model a set of inputs against desired outputs or classifications.

As previously discussed, there may be many different types of anomaly subsets that can be identified from the iteration data. Machine-learning techniques may be used for multiple purposes; they can be used to identify variability across data items of the same type, such as variability with regard to processing times for a task, inconsistencies across data taken from different sources, and so forth. However, machine-learning techniques described herein may also be used to acertain the variability for portions of data (e.g., data corresponding to a specific lab, a client, a task, a sparse indicator) in order to determine if that variability across data items of the same type is within the norm. Upon determining that the variability across data items of the same type is outside the norm, the system may then attempt to determine the cause of that deviation.

A first example of determining an anomaly subset of data includes determining tasks for various iterations of the workflow that have a long processing time relative to the past processing times for completing that task, or have a long processing time relative (either normalized or unnormalized) to the processing times of one or more other tasks in the workflow.

In some embodiments, this can be done through the system monitoring data and/or communications that are indicative of a task start time and/or a task completion time for each task performed in an iteration of a workflow. From this information, a processing time or a turnaround time may be identified for each completed task in an iteration of a workflow. In other embodiments, the system may alternatively monitor data and/or communications that are directly indicative of the turnaround processing time of tasks performed in an iteration of the workflow. This allows processing times to be directly known for every task performed in every iteration of the workflow. In some of such embodiments, the set of processing times available for each iteration of the workflow in the iteration data is exemplified by the set of processing times 306 corresponding to a set of tasks as shown in the iteration data 350 of FIG. 3.

After the task processing times are known, either directly or indirectly, for various iterations of differing time periods, laboratories, clients, and so forth, the assessment system 105 may apply machine-learning techniques to analyze processing times across multiple iterations of the workflow at a population level. In other words, per-task processing times can be analyzed for any given task across multiple iterations of the workflow. In some embodiments, the assessment system 105 may use strictly the iteration data in order to perform unsupervised learning on processing times for a specific task performed in every iteration in order to classify large processing times for that task as outliers.

In some embodiments, a training data set can be supplied to the assessment system 105 that informs of typical processing times associated with that specific task. In some embodiments, this training data set may include data from previous, historical iterations of the workflow. In some embodiments, the assessment system 105 may identify average (or median or mode) completion time periods for individual tasks so as to identify tasks (or labs or entities) associated with workflow processing delay. The processing times may also be used to determine standard deviations of task processing times, a count of outlier processing times, as well as a percentage of tasks that have a processing time below a threshold. In some embodiments, assessment system 105 may identify backlog for individual tasks by identifying a number of "open" tasks within the iteration data for which a start time has been identified but no completion time is identified. The labs and/or entities associated with those backlogged tasks can then be identified through the origin identifiers or data-source variables associated with the iterations of those backlogged tasks.

In some embodiments, the assessment system 105 may determine, for each handling entity (e.g., laboratory, distribution device, reviewer, or physician) a portion of tasks completed by a first threshold time identified for a given task. Upon detecting that the portion exceeds a second threshold, an alert communication can be transmitted to user device 180 and/or a device of an associated entity. Alternatively, upon detecting that a particular handling entity is completing a given task with processing times that, on average, exceed a certain threshold, an alert communication can be transmitted to user device 180 and/or a device of an associated entity.

In some embodiments, the assessment system 105 may analyze processing times for multiple different tasks, such as to determine that a particular task has a long processing time relative to the processing times of one or more other tasks in the workflow. For example, the assessment system 105 may utilize supervised machine-learning techniques to determine that a first task, on average, takes approximately twice as much processing time as a second task due to a relationship between the first task and the second task. Upon detecting that a particular handling entity is performing the first task with processing times that are greatly exceeding twice the average processing time of the second task, an alert communication can be transmitted to user device 180 and/or a device of an associated entity.

For these example embodiments, the assessment system 105 may or may not perform a normalization when comparing processing times corresponding to a single type of task, or when comparing processing times of multiple different tasks. The assessment system 105 may normalize processing times based on the type of task being performed, the amount of data being processed, the quantity or complexity of the results being generated, and so forth. For example, a particular task may be constrained by a rate at which data can be processed (e.g., the task may take ten times as long to process if being performed on ten times the amount of data). Although performing that task on ten times the amount of data takes much longer in absolute terms, in relative terms a ten-fold processing time would be expected. However, a twenty-fold processing time may be considered unusual. In that situation, the assessment system 105 may normalize the processing times for that task based on the amount of data processed by that task, which may involve determining a mathematical relationship between the processing times and the amount of data processed (e.g., one unit of time per one unit of data).

Once the assessment system 105 identifies an anomaly subset of tasks taking too long to process, the assessment system 105 may generate a communication identifying that anomaly subset and transmit it to user device 180 and/or a device of an associated handling entity. This communication can be used to identify bottlenecks within the workflow and improve the efficiency of future iterations of the workflow. More specifically, the communication may identify an anomaly subset of processing times and their associated tasks that are suspected of deviating from normal process times, which may then be sent to a user in order to detect tasks (or laboratories, devices, time periods or geographies) associated with processing delays. In some embodiments, the communication may include statistics (e.g., means, medians) corresponding to processing times of each task in a workflow. Additional statistics may also be provided based on entity and/or iteration (or task) start times. For example, the average processing times for tasks performed by a certain entity may be compared to average processing times for that task across all entities represented in the iteration data. In some embodiments, a graphical representation or distribution may be presented in the communication that visually conveys processing times associated with various tasks and/or entities.

A second example of determining an anomaly subset of data includes determining that data from a first data origin/source is statistically or sufficiently different from data from a second data origin/source. This may be the result of data from different sources having different biases, units, and/or representation. These different biases or units can be introduced a number of ways; personnel may utilize different protocols and/or data interpretation techniques, which may again result in receipt of data at assessment system 105 that has different biases, units, variables, and so on. Or, data originating from a same device may, in time, exhibit different biases, units, and so on, as a result of a manipulation of a control of the device and/or equipment wear.

In some embodiments, the assessment system 105 may retrieve a set of genetic data for a first set of clients that supplied samples to the first data origin/source. In some of such embodiments, the assessment system 105 may retrieve that set of genetic data from the iteration data as seen in FIG. 3. This set of genetic data may include the client data sets for the first set of clients, as well as any characteristics associated with each client data set, such as the sparse indicators and their classifications for each client data set. In some embodiments, the assessment system 105 may also retrieve a set of similar genetic data for a second set of clients that supplied samples to the second data origin/source. In some embodiments, these sets of data may be retrieved by querying the iteration data using the first data origin/source and/or the second data origin/source for the origin identifier or as data-source variables. In some embodiments, a second, different source is not required. The data from a first data origin can be statistically compared to historical data provided from the first data source, or to a baseline or set of control data that is known to be accurate.

If the set of genetic data for the first set of clients and the set of genetic data for the second set of clients are both sufficiently large, such that they provide a robust statistical representation of the greater population, then the system may determine whether the first genetic data set is statistically different from the second genetic data set. For example, a statistical test (e.g., a t-test or ANOVA) can be used to determine whether a number of sparse indicators detected per subject is statistically different across the data sets. As another example, a clustering technique can identify whether numeric outputs (e.g., gene counts) from the first data set are predominately clustered in a cluster different than a predominate cluster of numeric outputs from the second data set. This example of unsupervised machine-learning can be used to quickly identify that the first data set and the second data set are statistically different.

When it is determined that the two data sets are statistically different, and that the statistical difference is not due to the data being reported in different scientific units, the system may be able to determine a normalization that can be applied to genetic data generated based on processing of samples by the first laboratory or device. The normalization can include, for example, a multiplicative or additive factor, variables in an exponential function, variables in a power function, etc. The normalization can be identified by, for example, fitting data (e.g., to identify a fit between the first and second data sets). In some embodiments, a communication may be generated that identifies the statistical difference between the first genetic data set and the second genetic data set. Additionally, the implementation may also involve the system identifying a reason that data from a data origin/source is statistically different from what is expected. To do so, the system may use machine-learning techniques and big-data analysis in order to detect trends in equipment outputs and/or differences in equipment outputs. For example, cluster analyses can identify trends in cluster centers or sizes and/or can identify clusters that correspond to or may represent differences between laboratories or pieces of equipment. The system may then perform actions based on the identified reason for data from a data origin/source being different from what is expected. For example, if the system detects faulty equipment (e.g., via outlier detection), the system may provide a communication or a recommendation to a user to fix that equipment. Or, if the system detects that the measurements from the faulty equipment are due to systematic error, the system may be able to automatically determine an appropriate normalization and apply those adjustments to correct those measurements.

However, if the data being received from the data origin/source is in the wrong scientific unit, the system may instead determine a set of conversion and/or normalization metrics to be applied to data, and then perform an automated unit conversion and/or normalization on one of the data sets so that both data sets are of the same units. In some cases, units may be provided in the data so the system may be able to quickly determine that the units for data from the two data sets do not match. Thus, in many embodiments, the system may use machine-learning to automatically determine the reason for errors in data received from a given laboratory or device, and then apply an adjustment (such as an automated unit conversion and/or normalization) in order to fix those errors.

It may be particularly useful to statistically compare data from a first data origin to historical data provided from that same data source, especially when the historical data is accepted as being accurate or free of errors. Typically, two sets of data from the same data origin should be statistically similar. However, it is possible for systematic error to arise over time as the result of miss-calibration or equipment wear. Thus, machine-learning methods such as clustering can be utilized in such a scenario to quickly determine the existence of any statistical differences, which can inform of whether the data source should be re-calibrated or replaced.

As previously mentioned, unsupervised learning can be used to directly compare data from the two data sources in order to determine whether there is indeed a statistical difference, and then the degree of that statistical difference can be determined. However, data from both data sources could be erroneous. In such cases, supervised machine-learning techniques could be used. A set of data considered to be the baseline can be used to train a model that can be used to determine whether data from any particular source statistically deviates from the baseline. This may be useful, for example, if there were a large number of data origins of the same make and model that could have experienced wear over time. The data from all of these data origins can be compared to baseline data for that make and model in order to quickly determine which of the data origins may need replacing or fixing.

A third example of determining an anomaly subset of data includes determining one or more sparse indicators in a plurality of sparse indicators that are to be validated. In the example workflows for analyzing genetic data from lab samples, a client data set can be compared against a reference data set in order to identify a plurality of sparse indicators, with the sparse indicators representing differences between the client data set and the reference data set. Frequently, the workflow may further attempt to classify each of the sparse indicators, such as classifying whether each of the sparse indicators is a deviation that is pathogenic in nature (e.g., that particular difference between the client data set and the reference data set may lead to increased probabilities of certain diseases arising). This classification can be performed using a lookup of existing knowledge or based on more complex methods, such as through a predictive model. Thus, this classification may not always be completely accurate due to errors that arise in identifying the sparse indicator, as well as classifying it.

In order to mitigate these errors, some sparse indicators are picked to be sent out for double-checking and confirmation. In some embodiments, the client data set may generated again using more expensive and more accurate equipment in order to double-check any sparse indicators that need to be confirmed. In some embodiments, an identified sparse indicator may be correct but the classification assigned to that sparse indicator may need to be double-checked. These types of validations may not necessarily require that the client data set be generated again. However, in either case, the validation of every single sparse indicator (either for accuracy or classification) would be inefficient and time—consuming. Instead, machine-learning techniques and big-data analysis can be used to selectively determine sparse indicators for validation. For example, a machine-learning model can be trained based on a number of inputs and characteristics of sparse indicators. This model can be used to determine which sparse indicators are predicted to be accurately identified and require no further validation. The model can also be used to select sparse indicators that likely need to be double-checked and validated for accuracy and/or classification. Since the validation of sparse indicators can be a task in the workflow, the selective prediction of an anomaly subset of sparse indicators that require additional validation—as opposed to subjecting all of the sparse indicators to validation—can improve the efficiency of that task and the overall workflow.

For example, in some embodiments, a sparse indicator may be identified, but the system may determine that there is low confidence associated with the known existence of that identified sparse indicator. For example, the system may have identified a sparse indicator that was not previously observed. In some of such embodiments, the system may determine that a confidence metric associated with the sparse indicator is below an absolute or relative threshold. In this example, the system may determine that the client data set or the reference data set are inaccurate, leading to inaccurate differences between those data sets and non-existing sparse indicators. In order to validate the sparse indicator, the system may request that an external system perform more accurate and more expensive measurements on the client data set in order to better determine the differences between the client data set and the reference data set.

As another example, in some embodiments, a sparse indicator may fail to be assigned to a bucket, or the sparse indicator may be assigned to a certain data bucket with a low confidence that the sparse indicator belongs in that data bucket (e.g., if the sparse indicator may be incorrectly classified as "pathogenic"). Alternatively, the assigned data bucket may contribute to a degree of likeliness that a client will transition into or experience a particular state (e.g., the client will be subject to a certain disease), but the system may determine that there is either low confidence that the sparse indicator will contribute to a degree of likeliness that a client will transition into or experience a particular state or that there is low confidence that the assigned data bucket contributes to that degree of likeliness. In this example, the system may determine that the data, criteria, or models used in assigning the sparse indicator to that specific data bucket are inaccurate. In order to validate the assignment of the sparse indicator, the system may request an external system assign the sparse indicator to a data bucket, or the system may request from external sources additional information that can be used to more-accurately assign the sparse indicator to a data bucket. In some of such embodiments, the additional information received from external sources for improving assignment accuracy can be updated into the assignment criteria or model in order to improve the accuracy of future assignments.

As another example, in some embodiments, the system may determine that the general probability of an identified sparse indicator occurring is low. This low probability can be associated with the general population, or with a population having similar characteristics as the client for which the sparse indicator is associated. For instance, the system may identify a specific sparse indicator having an unlikely 0.001% chance of occurring. In this example, the system may also determine that the client data set or the reference data set are inaccurate, leading to inaccurate differences between those data sets and non-existing sparse indicators. In order to validate the sparse indicator, the system may request that an external system perform more accurate and more expensive measurements on the client data set in order to better determine the differences between the client data set and the reference data set.

The use of machine-learning to perform selective validation of sparse indicators confers numerous technological benefits and improvements to the efficiency of the workflow. For example, it would be too resource-intensive and inefficient to validate all of the sparse indicators, especially when most of the identified sparse indicators do not need to be validated. Thus, only performing validations on sparse indicators that are determined by the machine-learning model to need validation greatly cuts down on the processing time associated with validating the sparse indicators, which optimizes performance of iterations of the workflow.

It should be noted that, in some embodiments, numerous machine-learning techniques or models may be combined or used together in order to detect multiple types of anomaly subsets of the iteration data. The iteration data may be quite expansive and provide all the necessary inputs needed by multiple machine-learning algorithms, such that it may be more efficient for the iteration data to be collected once to be used by multiple machine-learning algorithms. Thus, in some embodiments, all of the described examples of machine-learning techniques can be used together.

It should also be noted that the machine-learning techniques described herein can be used for multiple purposes. For instance, supervised machine-learning techniques can be used to predict output variables that are categories, such as "red" versus "blue" or "disease" versus "no disease". For example, in order to determine which sparse indicators to validated, a model can be trained with a training set for which all the sparse indicators had been validated along with the results of those validations, such as whether each sparse indicator actually existed or did not exist. Sparse indicators that were validated and confirmed to exist may serve as proxy data points for determining sparse indicators that do not need validation, whereas sparse indicators that were validated and confirmed to not exist may serve as proxy data points for determining sparse indicators that do not validation. Thus, the model may be able to classify sparse indicators as "needing validation" or "not needing validation", using inputs such as the location and identity of the sparse indicators, how common that sparse indicator is across a population of patients, quality metrics associated with the lab generating the data (such as the confidence level associated with generating the set of reads), the client's medical risk history, and so forth.

Alternatively, supervised machine-learning techniques can also be used to predict output variables that are expressed in numerical values. For example, instead of classifying sparse indicators as "needing validation" or "not needing validation", machine-learning techniques can be used to determine a consistency or confidence value associated with any sparse indicator using similar inputs such as the location and identity of the sparse indicators, how common that sparse indicator is across a population of patients, quality metrics associated with the lab generating the data (such as the confidence level associated with generating the set of reads), the client's medical risk history, and so forth. The confidence value for each sparse indicator may then be compared to various threshold values for determining whether that sparse indicator should be validated or not. As another example, machine-learning techniques can be used with a training set containing data points for the processing times needed for various tasks, as well as values for many input variables, such as task type, laboratory identifiers, device identifiers, time periods, geographies, the amount of data being processed for that task, characteristics of the client and their medical risk history, and so forth. From this data, a model can be used to predict an estimated processing time that a task should take based on various input variables. The estimated processing time can be compared in some manner to the actual processing time for that task in order to make a determination for whether the task took too much time to perform.

Additionally, unsupervised machine-learning techniques can be used for numerous different purposes as well. For instance, unsupervised machine-learning techniques based on clustering can be used to discover inherent groupings in the data and learn more about hidden relationships that may exist. These groupings can be used for classification purposes. For example, unsupervised machine-learning algorithms can be used on iteration data to sort processing times for a given task into groups using clustering based on various data points that include values for patient identifiers, lab or device identifiers, time periods, geographies, and so forth. This can be used to uncover inherent groupings beyond grouping processing times that are normal and processing times that are taking too long. For example, the algorithm may determine there are actually three clusters— one cluster for normal processing times, and two different clusters for abnormal processing times. This information may signal the existence of hidden relationships in the data that can a user can attempt to seek explanations for. For example, one of the clusters for abnormal processing times may be the result of the task being performed on very large data sets, while the other cluster for abnormal processing times may be the result of the task being performed at a certain laboratory. Thus, in order to reduce abnormal processing times for the task, numerous actions would need to be taken.

Alternatively, unsupervised machine-learning techniques can be used to specifically to discover associations, such as hidden variables, rules, or relationships that describe large portions of the data. In these implementations, these hidden relationships may be more important than the quality of any output variable. This approach may be especially useful for circumstances in optimizing the efficiency of the workflow is a goal, since it provides insight and explanation for the reasons why certain tasks of the workflow are taking a long time. More specifically, this approach may allow a user to determine where hang-ups are occurring in the laboratory in order to improve the workflow. For example, an unsupervised machine-learning algorithm can be used to consider a large volume of data, such as iteration data, which would contain data for task processing times and task identifiers, patient identifiers, lab or device identifiers, patient characteristics or medical history, the amount of data being processed by the task, time periods, geographies, position and identities of sparse indicators, and so forth. The algorithm may then determine hidden relationships between variables. For example, the algorithm may determine that processing times for a certain task exponentially increase once the amount of data being processed by the task exceeds a certain level. This may suggest that, for that specific task, additional computing resources may need to be provided in order to reduce the bottleneck. Or, the algorithm may determine that processing times for a certain task may increase for a certain population of clients, since that population may be associated with certain sparse indicators that occur infrequently and take longer times to validate. Or, the algorithm may determine that processing times for a specific task are actually proportional or dependent on an earlier task within the workflow, so that in order the reduce processing times for that particular task, the processing times for the earlier task would have to be reduced. As another example, an unsupervised machine-learning algorithm may be used to determine associations for the selective confirmation of sparse indicators. Such an algorithm may consider a large volume of data, such as iteration data, which would contain data for patient identifiers, lab or device identifiers, patient characteristics or medical history, the amount of data being processed by the task, time periods, geographies, position and identities of sparse indicators, quality metrics associated with the lab, confidence levels associated with data obtained from the lab, confidence levels associated with the sparse indicators, and so forth. The more data items provided to the algorithm, the more the algorithm would consider; providing data for client age, for example, may prevent a certain lab that specializes in older clients from being penalized if the data from that lab is different from data associated with a wider-aged population. This algorithm may then determine the associations and relationships inherent in the data that would be useful in understanding why certain sparse indicators should be validated. For example, the algorithm may discover how the validation of specific sparse indicators may be dependent on the lab generating the data, the confidence level associated with that sparse indicator, a client's medical risk history, a quality metric associated with the lab, or how common that specific sparse indicator is across a population. For instance, the algorithm may determine that for a set of aligned reads received from a lab, the more of those reads that are identical at a given position, the less need there is to validate any sparse indicators based off those set of reads. Or, the algorithm may determine that sparse indicators should be validated if the sparse indicator occurs infrequently and the client associated with that sparse indicator has a medical risk history for a certain disease. Furthermore, the algorithm may be able to determine the influence or weight of these associations and variables. For instance, the algorithm may determine that the lab's identifier may not be impactful (or be much less impactful) on whether a sparse indicator should be validated, especially in comparison to a client's medical risk history. This may suggest that data obtained from the different labs may be rather consistent in quality and consideration should be placed elsewhere. These hidden variables, rules, or relationships can all be accounted for by the algorithm and provided to a user to gain a better understanding of how errors in the workflow can be reduced, and how the efficiency of the workflow can be improved.

Once the system has identified the appropriate anomaly subset of the iteration data, at block 534, the assessment system 105 may generate a report or communication that identifies the anomaly subset of the iteration data. A report transmission 518 is provided to the client 125 or facility 120 with the communication, although it may be transmitted to any entity that has control over the tasks performed in the workflow. The communication may identify specific bottlenecks in the workflow, as well as any sources of error in the data used in the workflow, depending on the anomaly subset of the iteration data identified. In some embodiments, the communication may also provide suggestions on how the efficiency of the workflow may be improved, or how any identified sources of error can be dealt with. The assessment system 105 may then receive feedback 520 from the client 125 or facility 120. This feedback 520 may identify whether the anomaly subset of the iteration data identified by the system is accurate, whether the recommendations or suggestions provided by the system are accurate, and so forth.

At block 536, the system may then utilize the received feedback in roder to update any machine-learning model used so that future identifications of anomaly subsets are improved and more accurate.

Alternative Implementations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method for using machine learning to identify anomaly subsets of sets of iteration data, the method comprising:
   accessing a structure including at least part of a definition for a workflow, the workflow including:
      a first task of aligning each read of a set of reads to a portion of a reference data set, wherein the reference data set includes a reference sequence;
      a second task of generating a client data set for the respective client using the aligned set of reads, the client data set including a set of values associated with each of one or more units, wherein the client data set includes a client sequence, wherein each value of the set of values represents a base, each unit of the one or more units representing a gene and corresponding to a set of defined positions within a genomic data structure; and
      a third task of detecting a presence of one or more sparse indicators associated with the respective client by comparing the set of values of the client data set to corresponding values in the reference data set, each sparse indicator of the one or more sparse indicators representing a variant indicative of a distinction between the client data set and the reference data set;
   for each client of a plurality of clients:
      accessing a set of reads based on a material associated with a respective client, wherein the material includes a biological material;
      performing an iteration of the workflow using the set of reads; generating iteration data based on the performance of the iteration of the workflow, wherein the iteration data includes or is based on:
         a result of a task in the workflow;

a time required to perform one or more tasks in the workflow;
and/or
a degree of usage of a computational resource while performing one or more tasks in the workflow;
storing the iteration data in association with an identifier of the client;
collecting a set of iteration data by retrieving, for each client of the plurality of clients, at least part of the stored iteration data;
using a machine-learning technique to process the set of iteration data to identify an anomaly subset of the set of iteration data; and
generating a communication that represents the anomaly subset.

2. The computer-implemented method for using machine learning to identify anomaly subsets of sets of iteration data as recited in claim 1, wherein:
the iteration data includes, for each task of a plurality of tasks of the workflow, a processing-time variable that indicates when a performance of the task was completed or a duration of performance of the task; and
the anomaly subset of the set of iteration data identified using the machine-learning technique identifies a task of the plurality of tasks associated with long processing times relative to past processing times or normalized or unnormalized processing times of one or more other tasks of the plurality of tasks.

3. The computer-implemented method for using machine learning to identify anomaly subsets of sets of iteration data as recited in claim 1, wherein:
the iteration data identifies one or more sparse indicators associated the client, such that the set of iteration data identifies a plurality of sparse indicators;
the anomaly subset of the set of iteration data identified using the machine-learning technique identifies a subset of the plurality of sparse indicators; and
the communication facilitates selective confirmatory processing to be performed to determine whether data corresponding to the subset of the plurality of sparse indicators is validated.

4. The computer-implemented method for using machine learning to identify anomaly subsets of sets of iteration data as recited in claim 1, wherein:
the iteration data further includes, for each client of the plurality of clients, an origination identifier associated with a source of the set of reads and a timestamp;
using the machine-learning technique to process the set of iteration data includes determining that results corresponding to a first origination identifier are statistically different than results corresponding to one or more second origination identifiers or than results corresponding to a prior time period and the first origination identifier; and
the communication identifies the source associated with the first origination identifier.

5. The computer-implemented method for using machine learning to identify anomaly subsets of sets of iteration data as recited in claim 1, wherein:
the iteration data further includes one or more data-source variables that identify or characterize a source of the iteration data; and
using the machine-learning technique includes updating or generating a model to identify data-source variables predictive of the result.

6. The computer-implemented method for using machine learning to identify anomaly subsets of sets of iteration data as recited in claim 1, wherein using the machine-learning technique comprises:
for each portion of multiple portions:
retrieving a parameter for a machine-learning model trained on another set of iteration data, the parameter reflecting a degree of variability observed in the another set of iteration data across clients or iterations;
generating an observed variability for the portion using the set of iteration data that reflects a degree of variability observed in the set of iteration data across clients or iterations;
determining whether the observed variability for the portion corresponds with the parameter; and
for each portion of the multiple portions for which it is determined that the observed variability for the portion does not correspond with the parameter, identifying the portion in the anomaly subset.

7. The computer-implemented method for using machine learning to identify anomaly subsets of sets of iteration data as recited in claim 1, further comprising:
receiving, from a source, a request to perform an anomaly-detection assessment, wherein the set of iteration data is collected and processed in response to receiving the request; and
availing the communication to the source.

8. A system for using machine learning to identify anomaly subsets of sets of iteration data, the system comprising:
one or more data processors; and
a non-transitory computer readable storage medium containing instructions which when executed on the one or more data processors, cause the one or more data processors to perform actions including:
accessing a structure including at least part of a definition for a workflow, the workflow including:
a first task of aligning each read of a set of reads to a portion of a reference data set, wherein the reference data set includes a reference sequence;
a second task of generating a client data set for the respective client using the aligned set of reads, the client data set including a set of values associated with each of one or more units, wherein the client data set includes a client sequence, wherein each value of the set of values represents a base, each unit of the one or more units representing a gene and corresponding to a set of defined positions within a genomic data structure; and
a third task of detecting a presence of one or more sparse indicators associated with the respective client by comparing the set of values of the client data set to corresponding values in the reference data set, each sparse indicator of the one or more sparse indicators representing a variant indicative of a distinction between the client data set and the reference data set;
for each client of a plurality of clients:
accessing a set of reads based on a material associated with a respective client, wherein the material includes a biological material;
performing an iteration of the workflow using the set of reads;
generating iteration data based on the performance of the iteration of the workflow, wherein the iteration data includes or is based on:
a result of a task in the workflow;

a time required to perform one or more tasks in the workflow;
and/or
a degree of usage of a computational resource while performing one or more tasks in the workflow;
storing the iteration data in association with an identifier of the client;
collecting a set of iteration data by retrieving, for each client of the plurality of clients, at least part of the stored iteration data;
using a machine-learning technique to process the set of iteration data to identify an anomaly subset of the set of iteration data; and
generating a communication that represents the anomaly subset.

9. The system for using machine learning to identify anomaly subsets of sets of iteration data as recited in claim 8, wherein:
the iteration data includes, for each task of a plurality of tasks of the workflow, a processing-time variable that indicates when a performance of the task was completed or a duration of performance of the task; and
the anomaly subset of the set of iteration data identified using the machine-learning technique identifies a task of the plurality of tasks associated with long processing times relative to past processing times or normalized or unnormalized processing times of one or more other tasks of the plurality of tasks.

10. The system for using machine learning to identify anomaly subsets of sets of iteration data as recited in claim 8, wherein:
the iteration data identifies one or more sparse indicators associated the client, such that the set of iteration data identifies a plurality of sparse indicators;
the anomaly subset of the set of iteration data identified using the machine-learning technique identifies a subset of the plurality of sparse indicators; and
the communication facilitates selective confirmatory processing to be performed to determine whether data corresponding to the subset of the plurality of sparse indicators is validated.

11. The system for using machine learning to identify anomaly subsets of sets of iteration data as recited in claim 8, wherein:
the iteration data further includes, for each client of the plurality of clients, an origination identifier associated with a source of the set of reads and a timestamp;
using the machine-learning technique to process the set of iteration data includes determining that results corresponding to a first origination identifier are statistically different than results corresponding to one or more second origination identifiers or than results corresponding to a prior time period and the first origination identifier; and
the communication identifies the source associated with the first origination identifier.

12. The system for using machine learning to identify anomaly subsets of sets of iteration data as recited in claim 8, wherein:
the iteration data further includes one or more data-source variables that identify or characterize a source of the iteration data; and
using the machine-learning technique includes updating or generating a model to identify data-source variables predictive of the result.

13. The system for using machine learning to identify anomaly subsets of sets of iteration data as recited in claim 8, wherein using the machine-learning technique comprises:
for each portion of multiple portions:
retrieving a parameter for a machine-learning model trained on another set of iteration data, the parameter reflecting a degree of variability observed in the another set of iteration data across clients or iterations;
generating an observed variability for the portion using the set of iteration data that reflects a degree of variability observed in the set of iteration data across clients or iterations;
determining whether the observed variability for the portion corresponds with the parameter; and
for each portion of the multiple portions for which it is determined that the observed variability for the portion does not correspond with the parameter, identifying the portion in the anomaly subset.

14. The system for using machine learning to identify anomaly subsets of sets of iteration data as recited in claim 8, wherein the actions further include:
receiving, from a source, a request to perform an anomaly-detection assessment, wherein the set of iteration data is collected and processed in response to receiving the request; and
availing the communication to the source.

15. A computer-program product tangibly embodied in a non-transitory machine-readable storage medium, including instructions configured to cause one or more data processors to perform actions including:
accessing a structure including at least part of a definition for a workflow, the workflow including:
a first task of aligning each read of a set of reads to a portion of a reference data set, wherein the reference data set includes a reference sequence;
a second task of generating a client data set for the respective client using the aligned set of reads, the client data set including a set of values associated with each of one or more units, wherein the client data set includes a client sequence, wherein each value of the set of values represents a base, each unit of the one or more units representing a gene and corresponding to a set of defined positions within a genomic data structure; and
a third task of detecting a presence of one or more sparse indicators associated with the respective client by comparing the set of values of the client data set to corresponding values in the reference data set, each sparse indicator of the one or more sparse indicators representing a variant indicative of a distinction between the client data set and the reference data set;
for each client of a plurality of clients:
accessing a set of reads based on a material associated with a respective client, wherein the material includes a biological material;
performing an iteration of the workflow using the set of reads; generating iteration data based on the performance of the iteration of the workflow, wherein the iteration data includes or is based on:
a result of a task in the workflow;
a time required to perform one or more tasks in the workflow;
and/or
a degree of usage of a computational resource while performing one or more tasks in the workflow;

storing the iteration data in association with an identifier of the client;

collecting a set of iteration data by retrieving, for each client of the plurality of clients, at least part of the stored iteration data;

using a machine-learning technique to process the set of iteration data to identify an anomaly subset of the set of iteration data; and generating a communication that represents the anomaly subset.

16. The computer-program product as recited in claim 15, wherein:

the iteration data includes, for each task of a plurality of tasks of the workflow, a processing-time variable that indicates when a performance of the task was completed or a duration of performance of the task; and the anomaly subset of the set of iteration data identified using the machine-learning technique identifies a task of the plurality of tasks associated with long processing times relative to past processing times or normalized or unnormalized processing times of one or more other tasks of the plurality of tasks.

17. The computer-program product as recited in claim 15, wherein:

the iteration data identifies one or more sparse indicators associated the client, such that the set of iteration data identifies a plurality of sparse indicators;

the anomaly subset of the set of iteration data identified using the machine-learning technique identifies a subset of the plurality of sparse indicators; and the communication facilitates selective confirmatory processing to be performed to determine whether data corresponding to the subset of the plurality of sparse indicators is validated.

18. The computer-program product as recited in claim 15, wherein:

the iteration data further includes, for each client of the plurality of clients, an origination identifier associated with a source of the set of reads and a timestamp;

using the machine-learning technique to process the set of iteration data includes determining that results corresponding to a first origination identifier are statistically different than results corresponding to one or more second origination identifiers or than results corresponding to a prior time period and the first origination identifier; and the communication identifies the source associated with the first origination identifier.

19. The computer-program product as recited in claim 15, wherein:

the iteration data further includes one or more data-source variables that identify or characterize a source of the iteration data; and using the machine-learning technique includes updating or generating a model to identify data-source variables predictive of the result.

20. The computer-program product as recited in claim 15, wherein using the machine-learning technique comprises:

for each portion of multiple portions:

retrieving a parameter for a machine-learning model trained on another set of iteration data, the parameter reflecting a degree of variability observed in the another set of iteration data across clients or iterations;

generating an observed variability for the portion using the set of iteration data that reflects a degree of variability observed in the set of iteration data across clients or iterations;

determining whether the observed variability for the portion corresponds with the parameter; and for each portion of the multiple portions for which it is determined that the observed variability for the portion does not correspond with the parameter, identifying the portion in the anomaly subset.

* * * * *